United States Patent
Cortopassi et al.

(10) Patent No.: US 9,750,705 B2
(45) Date of Patent: Sep. 5, 2017

(54) AGENTS USEFUL FOR TREATING OBESITY, DIABETES AND RELATED DISORDERS

(71) Applicant: The Regents of the University of California, Oakland, CA (US)

(72) Inventors: Gino Cortopassi, Davis, CA (US); Alexey Tomilov, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/424,422

(22) PCT Filed: Aug. 30, 2013

(86) PCT No.: PCT/US2013/057729
§ 371 (c)(1),
(2) Date: Feb. 26, 2015

(87) PCT Pub. No.: WO2014/036528
PCT Pub. Date: Mar. 6, 2014

(65) Prior Publication Data
US 2015/0216819 A1    Aug. 6, 2015

Related U.S. Application Data

(60) Provisional application No. 61/696,112, filed on Aug. 31, 2012.

(51) Int. Cl.
| | |
|---|---|
| *A61K 31/122* | (2006.01) |
| *A61K 38/08* | (2006.01) |
| *G01N 33/74* | (2006.01) |
| *A61K 31/155* | (2006.01) |
| *A61K 31/198* | (2006.01) |
| *A61K 31/4184* | (2006.01) |
| *A61K 31/702* | (2006.01) |
| *A61K 31/194* | (2006.01) |
| *A61K 31/277* | (2006.01) |
| *A61K 31/4015* | (2006.01) |
| *A61K 31/42* | (2006.01) |
| *A61K 31/426* | (2006.01) |
| *A61K 31/4402* | (2006.01) |
| *A61K 31/4745* | (2006.01) |
| *A61K 31/496* | (2006.01) |
| *A61K 31/517* | (2006.01) |
| *G01N 33/573* | (2006.01) |

(52) U.S. Cl.
CPC .......... *A61K 31/122* (2013.01); *A61K 31/155* (2013.01); *A61K 31/194* (2013.01); *A61K 31/198* (2013.01); *A61K 31/277* (2013.01); *A61K 31/4015* (2013.01); *A61K 31/4184* (2013.01); *A61K 31/42* (2013.01); *A61K 31/426* (2013.01); *A61K 31/4402* (2013.01); *A61K 31/4745* (2013.01); *A61K 31/496* (2013.01); *A61K 31/517* (2013.01); *A61K 31/702* (2013.01); *A61K 38/08* (2013.01); *G01N 33/573* (2013.01); *G01N 33/74* (2013.01); *G01N 2333/912* (2013.01); *G01N 2440/14* (2013.01)

(58) Field of Classification Search
CPC ................................................... A61K 31/122
USPC ......................................................... 552/296
See application file for complete search history.

(56) References Cited

U.S. PATENT DOCUMENTS

| | | | |
|---|---|---|---|
| 5,962,535 A | 10/1999 | Miyamoto et al. | |
| 6,133,322 A | 10/2000 | Rustin et al. | |
| 7,981,915 B2 | 7/2011 | Freedman | |
| 8,062,679 B2 | 11/2011 | Clement et al. | |
| 8,293,290 B2 | 10/2012 | Tan | |
| 8,741,853 B2 | 6/2014 | Steliou | |
| 2003/0077335 A1* | 4/2003 | Richardson | A61K 31/198 424/682 |
| 2003/0219377 A1 | 11/2003 | Raub et al. | |
| 2004/0067986 A1 | 4/2004 | Sassover | |
| 2005/0107386 A1* | 5/2005 | Narla | A61K 31/4196 514/243 |
| 2006/0094682 A1* | 5/2006 | Westwick | C12Q 1/485 514/44 A |
| 2006/0264384 A1 | 11/2006 | Johnson et al. | |
| 2007/0259837 A1 | 11/2007 | Meier et al. | |
| 2008/0096915 A1 | 4/2008 | Cornett et al. | |
| 2008/0262088 A1 | 10/2008 | Hauck et al. | |

(Continued)

FOREIGN PATENT DOCUMENTS

| | | |
|---|---|---|
| CN | 101 273 994 A | 10/2008 |
| CN | 101 278 940 A | 10/2008 |

(Continued)

OTHER PUBLICATIONS

EP patent application No. 13833754.8, Supplementary Partial European Search Report mailed May 2, 2016.
Aicher, Thomas D. et al., "Secondary amides of (R)-3,3,3-trifluoro-2hydroxy-2-methylpropionic acid as inhibitors of pyruvate dehydrogenase kinase," *J. Med. Chem.* 2000, 43, 236-249.
Database WPI, week 200748, Thomson Scientific, "Novelty: a blood flowability improving agent contains ornithine or its salt as active ingredient." May 3, 2007. XP-002755847.
Database WPI, week 200827, Thomson Scientific, "Novelty: composition for health food, contains component having anorectic effect, component having digestive enzyme activation inhibitory effect, components containing chitosan and component containing dietary fiber." Dec. 27, 2007 XP-002755846.

(Continued)

*Primary Examiner* — David Lukton
(74) *Attorney, Agent, or Firm* — Weaver Austin Villeneuve & Sampson LLP

(57) ABSTRACT

This invention provides methods of identifying agents useful to prevent, ameliorate or treat one or more symptoms of impaired insulin sensitivity, glucose tolerance, obesity, diabetes, aging, metabolic syndrome, or other metabolic syndrome component diseases, and methods of employing the identified agents to prevent, reduce, delay or inhibit one or more symptoms of impaired insulin sensitivity, glucose tolerance, obesity, diabetes, aging, metabolic syndrome, or other metabolic syndrome component diseases.

20 Claims, 7 Drawing Sheets

(56) References Cited

U.S. PATENT DOCUMENTS

| | | | |
|---|---|---|---|
| 2009/0060993 A1 | 3/2009 | Schwarz et al. | |
| 2009/0208425 A1 | 8/2009 | Debach-Powell et al. | |
| 2010/0029706 A1 | 2/2010 | Miller et al. | |
| 2010/0048454 A1* | 2/2010 | Arbit | A61K 38/28 514/1.1 |
| 2010/0130619 A1 | 5/2010 | Schwarz et al. | |
| 2010/0136127 A1 | 6/2010 | Yamamoto et al. | |
| 2010/0137278 A1* | 6/2010 | Allen | C07D 403/12 514/210.18 |
| 2010/0189819 A1 | 7/2010 | Sassover | |
| 2010/0239552 A1 | 9/2010 | Mayoux et al. | |
| 2010/0256061 A1* | 10/2010 | Cruz | A61K 31/155 514/6.9 |
| 2011/0207741 A1 | 8/2011 | Dudley | |
| 2011/0217371 A1 | 9/2011 | Shin et al. | |
| 2011/0263526 A1 | 10/2011 | Satyam | |
| 2012/0009259 A1 | 1/2012 | Delaet et al. | |
| 2012/0082719 A1 | 4/2012 | Ang | |
| 2012/0082720 A1 | 4/2012 | Ang | |
| 2012/0177730 A1 | 7/2012 | Baron et al. | |
| 2012/0178748 A1* | 7/2012 | Campbell | A61K 45/06 514/230.2 |
| 2013/0143840 A1 | 6/2013 | Parish et al. | |
| 2013/0189343 A1 | 7/2013 | Krumme et al. | |
| 2014/0044692 A1 | 2/2014 | Shchepinov | |
| 2014/0050728 A1 | 2/2014 | Padanilam | |
| 2014/0294724 A1 | 10/2014 | Chain | |
| 2014/0357602 A1 | 12/2014 | Mayoux et al. | |
| 2014/0370110 A1 | 12/2014 | Perumal et al. | |
| 2014/0377312 A1 | 12/2014 | Krumme et al. | |

FOREIGN PATENT DOCUMENTS

| | | |
|---|---|---|
| CN | 101 984 974 A | 3/2011 |
| CN | 102 218 062 B | 5/2013 |
| CN | 102 399 837 B | 7/2013 |
| CN | 102 266 388 B | 8/2014 |
| CN | 102 559 814 B | 11/2015 |
| EP | 475536 | 3/1992 |
| EP | 1662258 | 5/2006 |
| EP | 2620141 | 7/2013 |
| EP | 2727587 | 5/2014 |
| JP | 2007 330124 A | 12/2007 |
| WO | 00/19993 | 4/2000 |
| WO | 00/23568 | 4/2000 |
| WO | 02/064586 | 8/2002 |
| WO | WO 2007/049628 A1 | 5/2007 |
| WO | 2008/101344 | 8/2008 |
| WO | 2010/036794 | 4/2010 |
| WO | 2011/128782 | 10/2011 |
| WO | 2011/133668 | 10/2011 |
| WO | WO 2011/134962 A2 | 11/2011 |
| WO | WO 2012/008809 A2 | 1/2012 |
| WO | 2012/093972 | 7/2012 |
| WO | 2012/093973 | 7/2012 |
| WO | 2012/143041 | 10/2012 |
| WO | 2013/110442 | 8/2013 |
| WO | 2013/152039 | 10/2013 |
| WO | 2014/007775 | 1/2014 |
| WO | 2014/035355 | 3/2014 |
| WO | 2014/035356 | 3/2014 |
| WO | 2014/036528 | 3/2014 |
| WO | 2014/043230 | 3/2014 |
| WO | 2014/055047 | 4/2014 |
| WO | 2014/068007 | 5/2014 |
| WO | 2014/138922 | 9/2014 |
| WO | 2014/201155 | 12/2014 |
| WO | WO 2016/144829 A1 | 9/2016 |

OTHER PUBLICATIONS

Database WPI, week 200878, Thomson Scientific, "Novelty: a Chinese composition comprises (pts.wt.) arctiin (50-99) and arctigenin (1-50) having 90% purity." Oct. 8, 2008. XP-002755843.

Database WPI, week 200915, Thomson Scientific, "Novelty: pharmaceutical composition comprises (wt.%) arctiin (50-99) or arctigenin (1-50) having purity of over 90%." Oct. 1, 2008. XP-002755844.

Database WPI, week 201142, Thomson Scientific, "Novelty: method for preparing pharmaceutical composition, involves (a) preparing metformin hydrochloride tablet core by preparing the metformin hydrochloride and auxiliary materials required for tablet, coating the tablet core with semipermeable film layer and subjecting obtained product to laser to obtain tablet core, and (b) coating the tablet core with glimepiride by obtaining the glimepiride and auxiliary materials required for preparing coated liquid capable of dissolving in stomach, and coating the tablet core with the liquid." Mar. 16, 2011. XP-002755838.

Database WPI, week 201175, Thomson Scientific, "Novelty: orally disintegrating tablet (I) contains 1-30% of acarbose, 40-90% of water-soluble carrier, and 1-50% of water-insoluble carrier." Nov. 3, 2011. XP002755840.

Database WPI, week 201210, Thomson Scientific, "Novelty: a microorganism capable of producing L-ornithine in which gluconate kinase (GntK) activity is weakened relative to its intrinsic activity, is new." Jan. 19, 2012. XP-002755845.

Database WPI, week 201230, Thomson Scientific, "Novelty: medicinal composition comprises metformin hydrochloride and traditional Chinese medicine extract as active ingredients." Dec. 7, 2011. XP002755837.

Database WPI, week 201234, Thomson Scientific, "Novelty: a drug composition comprises active components of arctigenin and rosiglitazone or salt of rosiglitazone." Oct. 19, 2011. XP-002755842.

Database WPI, week 201256, Thomson Scientific, "Novelty: synthesizing acarbose by microbial fermentation, comprises inoculating acarbose producing strain CCTCC No. M209022 into fermentation medium containing carbon source, nitrogen source and inorganic salt, fermenting a culturing it for 96-192 hours at 20-32[deg] C., obtaining the fermentation liquor to extract and separating it after fermentation, and obtaining the acarbose, carrying out the fermentation cultivation for 0-60 hours, and adding a solution of ademetionine, where the concentration of the ademetionine in the fermentation medium is 1-300 mu mole/I." Apr. 4, 2012. XP-002755839.

Database WPI, week 201301, Thomson Scientific, "Novelty: preparing acarbose involves: (a) liquefying the starch emulsion with alpha-amylase under proper pH and temperature, controlling dextrose equivalent (DE) value of 11-18, and to obtain the liquefied liquid; (b) cooling the liquefied liquid to proper temperature, regulating pH properly, adding pullulanase, fungal enzyme, and beta-amylase, and keeping for 4-8 hours at 55-60° C. to obtain starch saccharified liquid; and (c) sterilizing the starch saccharified liquid and applying it to acarbose fermentation." Jul. 11, 2012. XP-002755841.

Jonas, Michael et al., "Vascular neointimal formation and signaling pathway activation in response to stent injury in insulin-resistant and diabetic animals," *Circulation Research*, Sep. 30, 2005, pp. 725-733.

Stebbins, John L., "Identification of a new JNK inhibitor targeting the JNK-JIP interaction site," *PNAS*, Oct. 28, 2008, vol. 105, No. 43, 16809-16813.

PCT International Search Report and Written Opinion dated Feb. 19, 2014 issued in PCT/US2013/057729.

PCT International Preliminary Report on Patentability dated Mar. 12, 2015 issued in PCT/US2013/057729.

European Extended Search Report dated Aug. 25, 2016 issued in Application No. EP 13 833 754.8.

PCT International Search Report and Written Opinion dated Aug. 18, 2016 issued in PCT/US2016/21070.

* cited by examiner

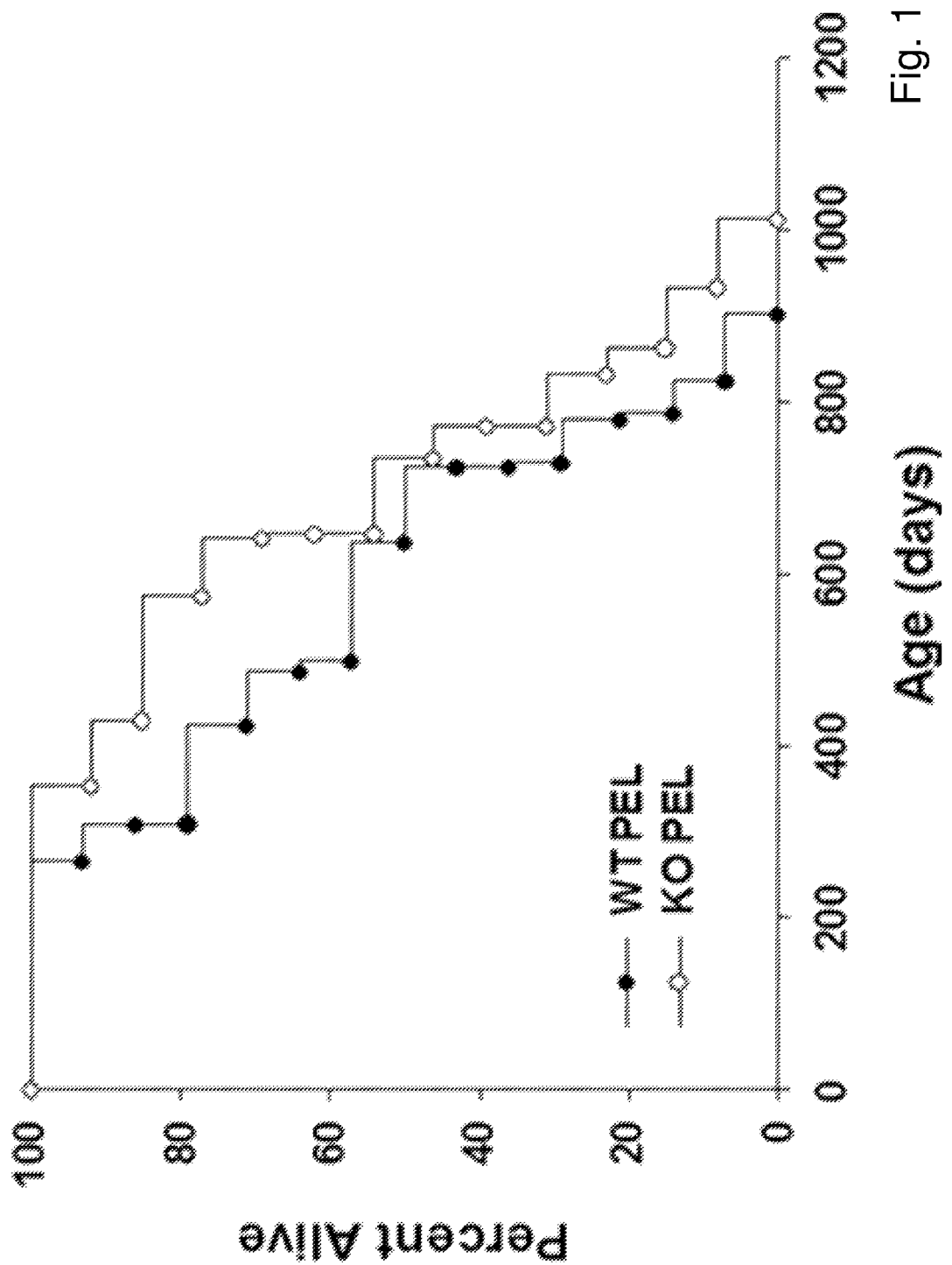

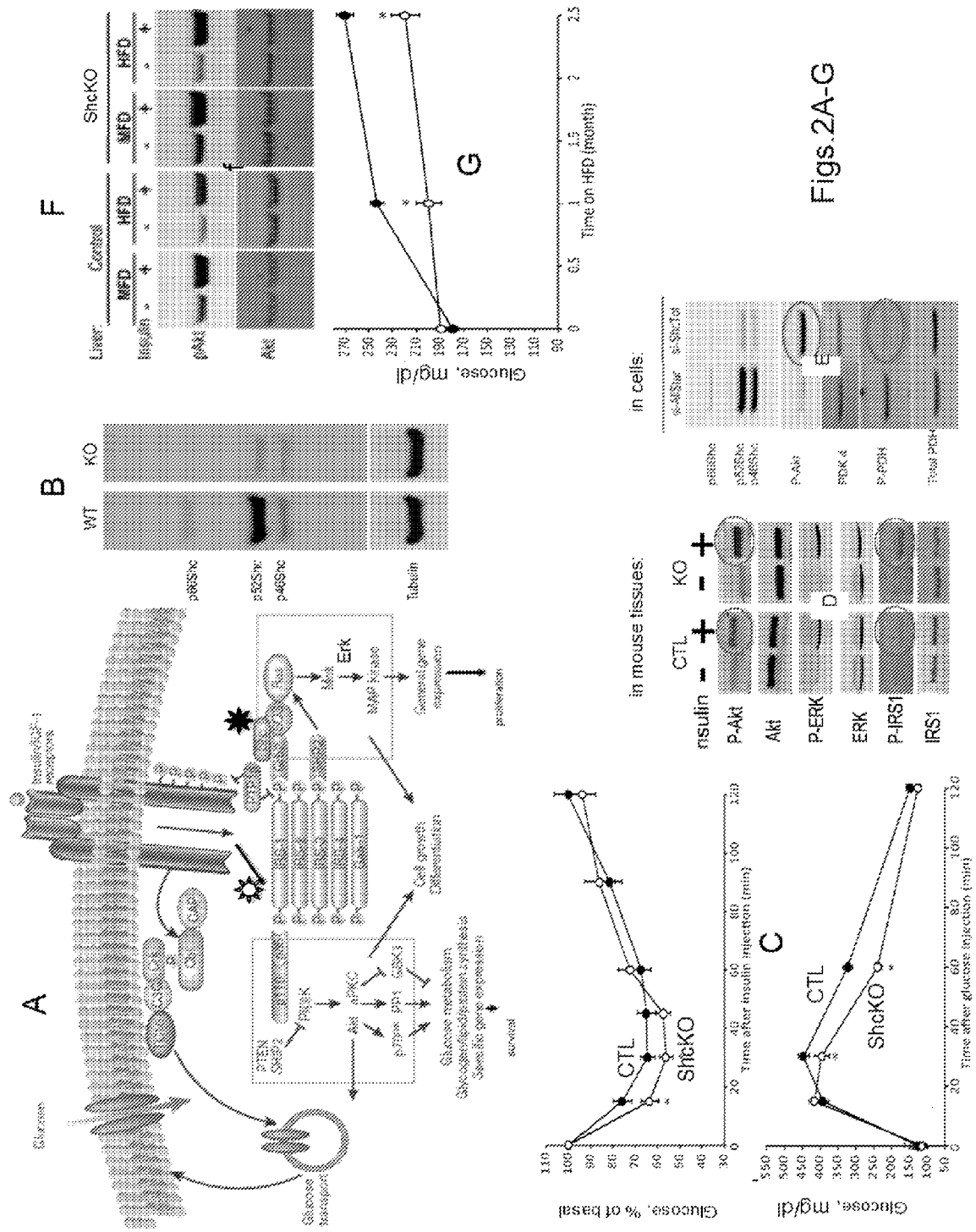
Figs. 2A-G

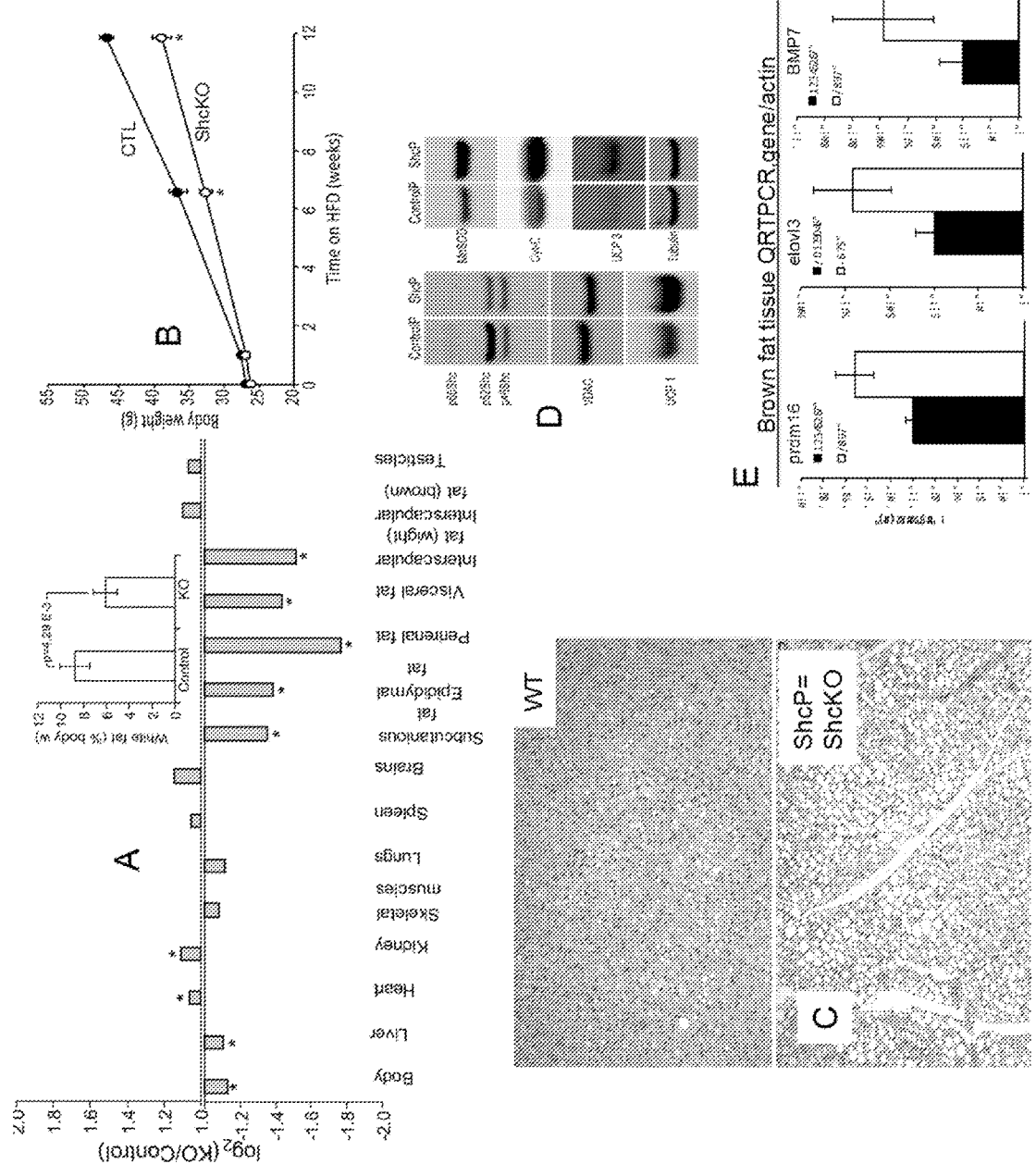
Figs. 3A-E

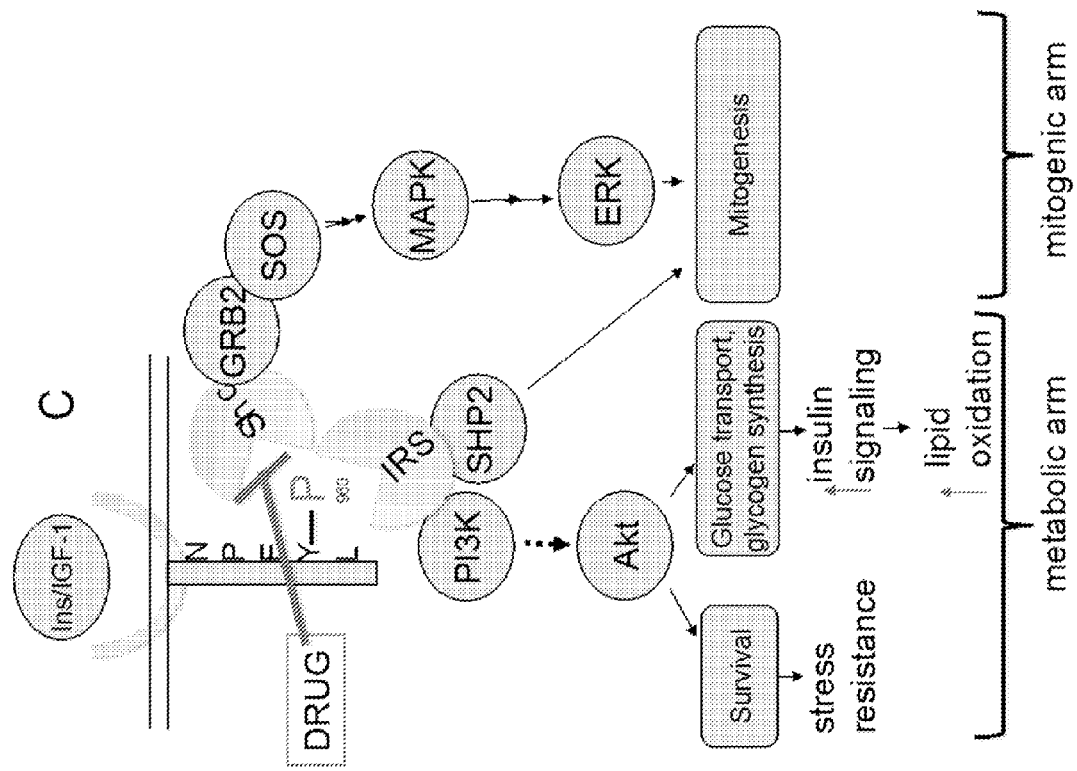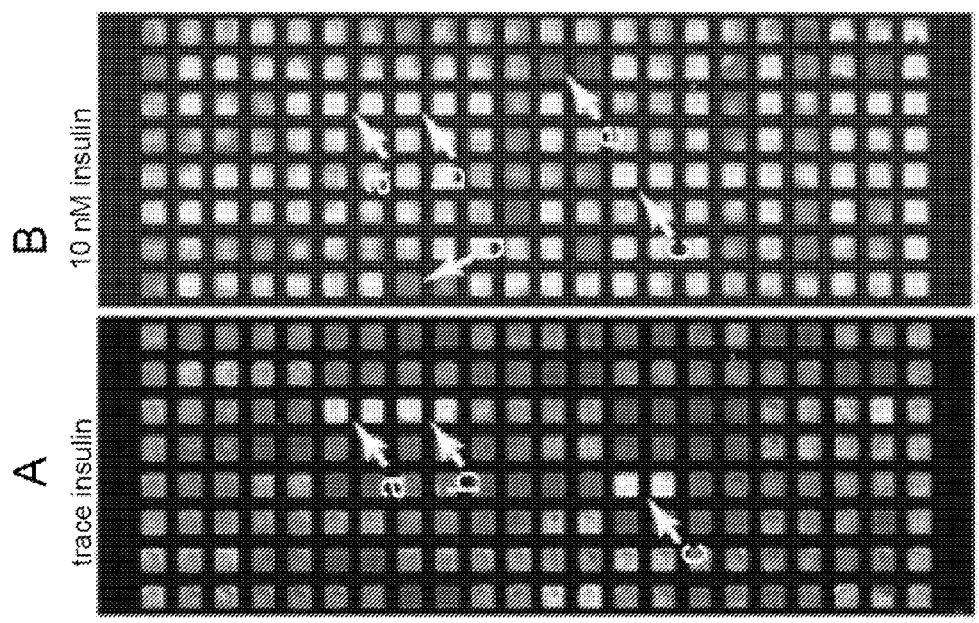
Figs. 4A-C

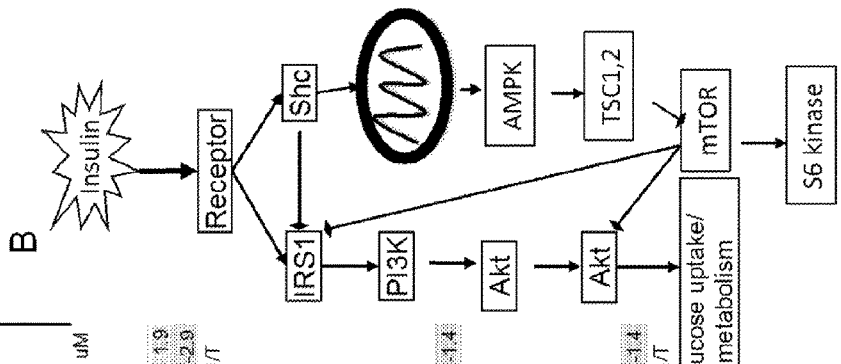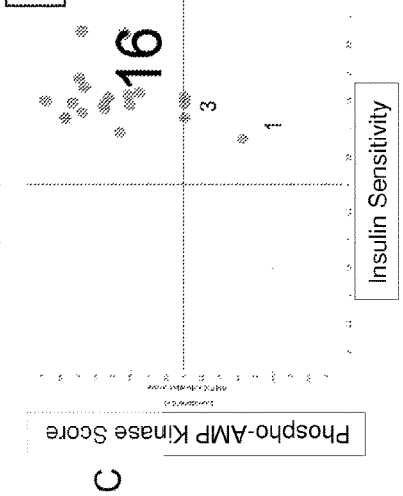
Figs. 5ABC

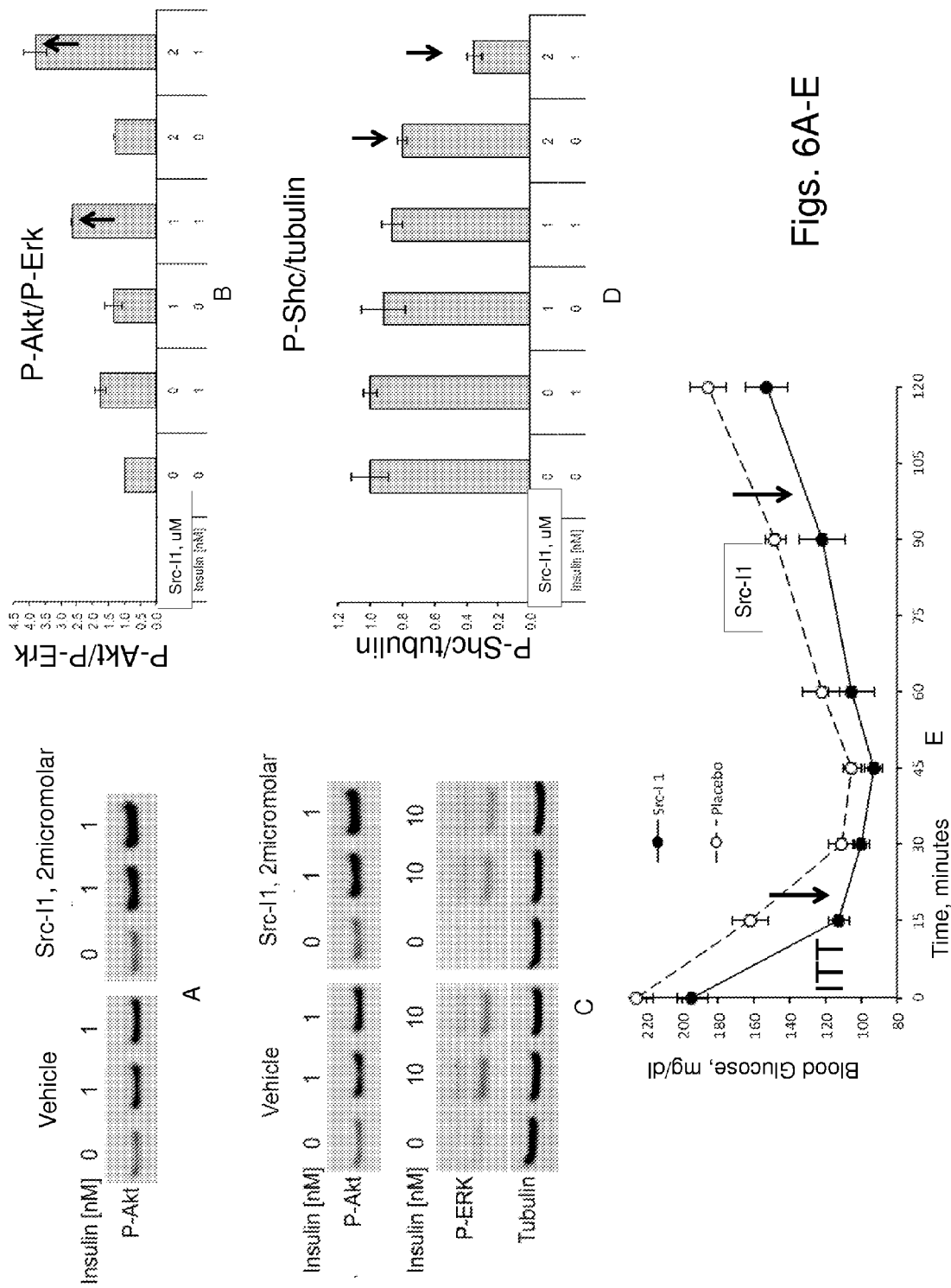
Figs. 6A-E

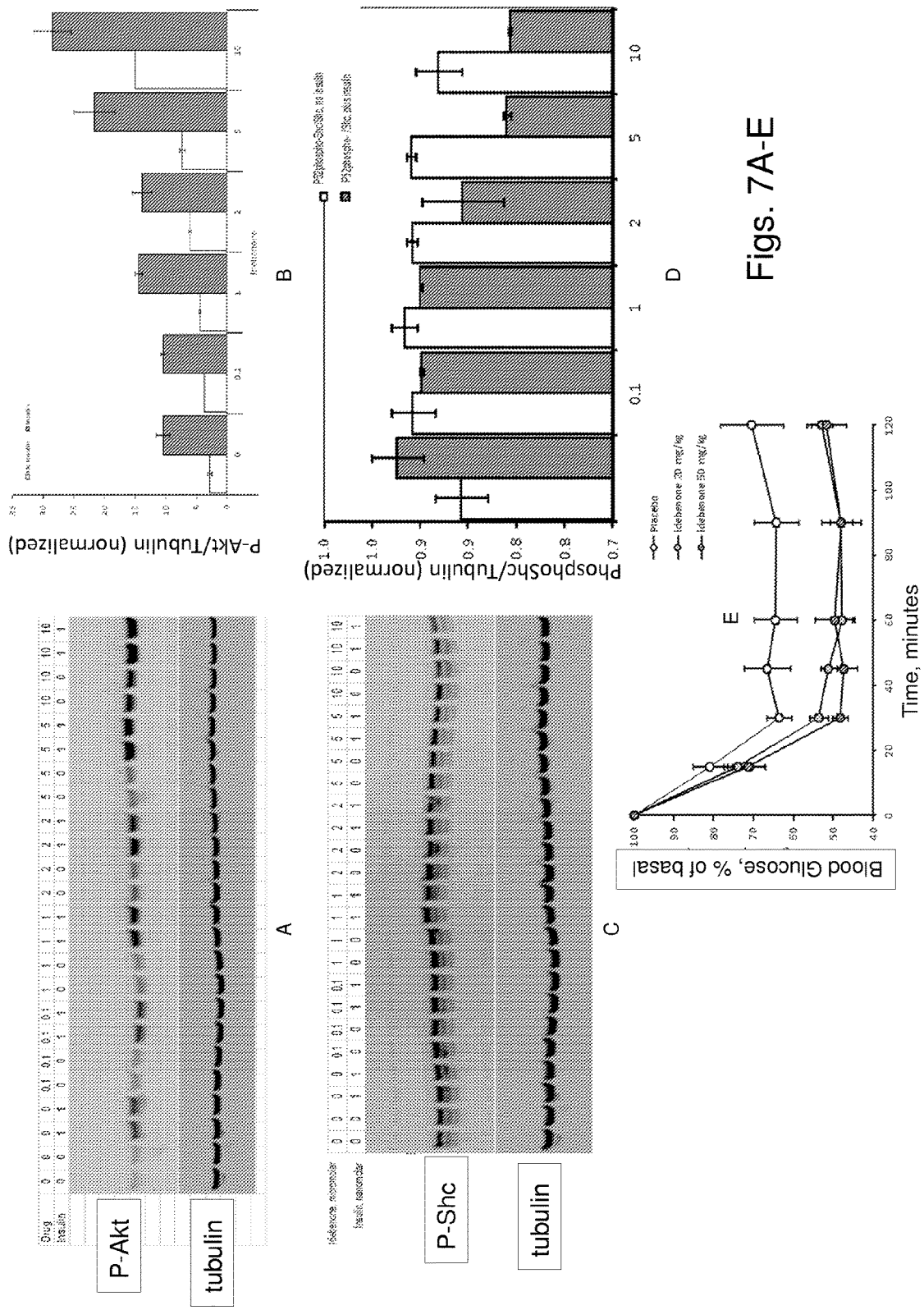
Figs. 7A-E

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Synthesized
<220> FEATURE:
<223> OTHER INFORMATION: ELOVL3-F

<400> SEQUENCE: 1
atgaactttg gcgtccattc                                               20

<210> SEQ ID NO 2
<211> LENGTH: 20
<212> TYPE: DNA
<213> ORGANISM: Artificial Sequence
<220> FEATURE:
<223> OTHER INFORMATION: Synthesized
<220> FEATURE:
<223> OTHER INFORMATION: ELOVL3-R

<400> SEQUENCE: 2
ctttctcctg cctccagatg                                               20
```

<210> SEQ ID NO 3
<211> LENGTH: 19
<212> TYPE: DNA
<213> ORGANISM: Artificial Sequence
<220> FEATURE:
<223> OTHER INFORMATION: Synthesized
<220> FEATURE:
<223> OTHER INFORMATION: Prdm16-F

<400> SEQUENCE: 3
cagcacggtg aagccattc                                                    19

<210> SEQ ID NO 4
<211> LENGTH: 17
<212> TYPE: DNA
<213> ORGANISM: Artificial Sequence
<220> FEATURE:
<223> OTHER INFORMATION: Synthesized
<220> FEATURE:
<223> OTHER INFORMATION: Prdm16-R

<400> SEQUENCE: 4
gcgtgcatcc gcttgtg                                                      17

<210> SEQ ID NO 5
<211> LENGTH: 20
<212> TYPE: DNA
<213> ORGANISM: Artificial Sequence
<220> FEATURE:
<223> OTHER INFORMATION: Synthesized
<220> FEATURE:
<223> OTHER INFORMATION: BMP7-F

<400> SEQUENCE: 5
cctgtccatc ttagggttgc                                                   20

<210> SEQ ID NO 6
<211> LENGTH: 21
<212> TYPE: DNA
<213> ORGANISM: Artificial Sequence
<220> FEATURE:
<223> OTHER INFORMATION: Synthesized
<220> FEATURE:
<223> OTHER INFORMATION: BMP7-R

<400> SEQUENCE: 6
gccttgtagg ggtaggagaa g                                                 21

<210> SEQ ID NO 7
<211> LENGTH: 20
<212> TYPE: DNA
<213> ORGANISM: Artificial Sequence
<220> FEATURE:
<223> OTHER INFORMATION: Synthesized
<220> FEATURE:
<223> OTHER INFORMATION: UCP1-F

<400> SEQUENCE: 7
gatggtgaac ccgacaactt                                                   20

<210> SEQ ID NO 8
<211> LENGTH: 20
<212> TYPE: DNA
<213> ORGANISM: Artificial Sequence
<220> FEATURE:
<223> OTHER INFORMATION: Synthesized
<220> FEATURE:

```
<223> OTHER INFORMATION: UCP1-R

<400> SEQUENCE: 8
ctgaaactcc ggctgagaag                                             20
```

AGENTS USEFUL FOR TREATING OBESITY, DIABETES AND RELATED DISORDERS

CROSS-REFERENCE TO RELATED APPLICATIONS

The present application is a US National Stage entry of PCT/US2013/057729 filed Aug. 30, 2013, which is a non-provisional of U.S. 61/696,112 filed Aug. 31, 2012, which is incorporated by reference in its entirety for all purposes.

REFERENCE TO A SEQUENCE LISTING

This application includes an electronic sequence listing in a file named 458562_SEQLST.TXT created on Feb. 26, 2015 and containing 1.95 kilobytes, which is hereby incorporated by reference.

BACKGROUND

Obesity and type 2 diabetes are common metabolic diseases frequently occurring together. Most patients with type 2 diabetes are or have been obese. Obesity increases the risk of developing type 2 diabetes about ten-fold (Field et al., Arch Intern Med, 161: 1581-6 (2001). The term Metabolic Syndrome has been coined to describe a cluster of interrelated common clinical disorders, including obesity, insulin resistance, glucose intolerance, hypertension and dyslipidemia (Reaven, (1988) Diabetes 37; 1595-1607). Metabolic syndrome, its components diseases and sequelae are a severe and increasing health problem world-wide (Zimmet et al., Obesity, 14:1-3, 2006).

SUMMARY OF THE CLAIMED INVENTION

The invention provides a method of treating or effecting prophylaxis of impaired insulin sensitivity, glucose tolerance or obesity, comprising administering to a subject having the impaired insulin sensitivity, glucose tolerance or obesity an effective regime of sulfisoxazole acetyl, metformin hydrochloride, pyronaridine tetraphosphate, azaperone, idebenone, acarbose, pefloxacine, candesartan cilexetil, cypermethrin, tripelennamine citrate, diperodon hydrochloride, aniracetam, fpa 124, methacycline hydrochloride, arctigenin, 10a, pyrithyldione, TBB, ornithine, 11e, 14e, Src I-1, BI 78D3, nitazoxanide, N-Acetyl-O-phosphono-Tyr-Glu-Glu-Ile-Glu, or a pharmaceutically acceptable salt thereof, thereby treating or effecting prophylaxis of the of impaired insulin sensitivity, glucose tolerance or obesity. Optionally, the subject has type 2 diabetes. Optionally, the subject has a body mass index of at least 30.

The invention also provides a method of treating or effecting prophylaxis of impaired insulin sensitivity or obesity, comprising administering to a subject having the impaired insulin sensitivity or obesity an effective regime of a Shc antagonist, thereby treating or effecting prophylaxis of the syndrome or disorder.

The invention further provides a method of treating or effecting prophylaxis of metabolic syndrome, comprising administering to a subject having or at risk of metabolic syndrome an effective regime of sulfisoxazole acetyl, metformin hydrochloride, pyronaridine tetraphosphate, azaperone, idebenone, acarbose, pefloxacine, candesartan cilexetil, cypermethrin, tripelennamine citrate, diperodon hydrochloride, aniracetam, fpa 124, methacycline hydrochloride, arctigenin, 10a, pyrithyldione, TBB, ornithine, 11e, 14e, Src I-1, BI 78D3, nitazoxanide, N-Acetyl-O-phosphono-Tyr-Glu-Glu-Ile-Glu, or a pharmaceutically acceptable salt thereof, thereby treating or effecting prophylaxis of the syndrome. Optionally, the subject has diabetes type 2. Optionally, the subject is obese. Optionally, the subject has impaired insulin sensitivity and glucose tolerance. Optionally, the subject has hyperglycemia. Optionally, the subject has dyslipidemia. Optionally, the subject has microalbuminuria.

The invention further provides a method of inhibiting aging, comprising administering to a subject an effective regime of sulfisoxazole acetyl, metformin hydrochloride, pyronaridine tetraphosphate, azaperone, idebenone, acarbose, pefloxacine, candesartan cilexetil, cypermethrin, tripelennamine citrate, diperodon hydrochloride, aniracetam, fpa 124, methacycline hydrochloride, arctigenin, 10a, pyrithyldione, TBB, ornithine, 11e, 14e, Src I-1, BI 78D3, nitazoxanide, N-Acetyl-O-phosphono-Tyr-Glu-Glu-Ile-Glu, or a pharmaceutically acceptable salt thereof, thereby inhibiting aging.

The invention further provides a method of screening a compound for an indication of an activity useful for treating impaired insulin sensitivity, glucose intolerance or obesity; comprising (a) exposing cells to the compound and insulin; (b) determining phosphorylation status of Akt1 and Erk, e.g. phospho-Akt1 and phospho-Erk; wherein an increased ratio of levels of phospho-Akt-1 over phospho-Erk relative to a control ratio provides an indication the compound has activity useful for treating impaired insulin sensitivity or obesity. Optionally, the method further comprises determining drug-dependent effects on mitochondrial physiology by measuring of mitochondrial oxygen consumption and proton production rates of cells employing the Seahorse XF 24 machine (cell metabolism analyzer). Optionally, the method further comprises determining drug-dependent effects on mitochondrial $O_2$ uptake using biosensor plates. Optionally, the method further comprises determining drug-dependent effects on mitochondria by assay of phospho-AMP kinase. Optionally, the method further comprises determining the drug's ability to inhibit or stimulate mitochondrial ATP synthesis. Optionally, the method further comprises the drug's ability to stimulate or inhibit mitochondrial membrane potential. Optionally, the method further comprises the drug's ability to rescue cells from intoxication with a mitochondrial-specific oxidant, diamide. Optionally, the method further comprises determining cytoxicity of drugs by tubulin polymerization assay. Optionally, the method further comprises screening the compound in an animal model of diabetes. Optionally, the method further comprises screening the compound in an animal model of obesity.

DEFINITIONS

The terms "individual," "patient," "subject" interchangeably refer to a mammal, for example, a human, a non-human primate, a domesticated mammal (e.g., a canine or a feline), an agricultural mammal (e.g., equine, bovine, ovine, porcine), or a laboratory mammal (e.g., rattus, murine, lagomorpha, hamster).

The terms "treating" and "treatment" refer to delaying the onset of, retarding or reversing the progress of, reducing the severity of, or alleviating or preventing either the disease or disorder to which the term applies, or one or more symptoms of such disease or disorder.

The term "effective amount" or "therapeutically effective amount" refers to the amount of an active agent sufficient to induce a desired biological result. That result may be alleviation of the signs, symptoms, or causes of a disease, or any other desired alteration of a biological system. The term "therapeutically effective amount" is used herein to denote any amount of the formulation which causes a substantial improvement in sign(s) or symptom(s) a disease or disorder when applied to the affected areas repeatedly over a period of time. The amount varies with the disease or disorder being treated, the stage of advancement of the disease or disorder, and the type and concentration of formulation applied.

A "therapeutic effect" encompasses a therapeutic benefit and/or a prophylactic benefit as described above. A prophylactic effect includes delaying or eliminating the appearance of a disease or disorder, delaying or eliminating the onset of symptoms of a disease or disorder, slowing, halting, or reversing the progression of a disease or disorder, or any combination thereof.

"Administering" refers to local or systemic administration, e.g., including enteral or parenteral administration. Routes of administration for the active agents that find use in the present invention include, e.g., oral ("po") administration, administration as a suppository, topical contact, intravenous ("iv"), intraperitoneal ("ip"), intramuscular ("im"), intralesional, intranasal, or subcutaneous ("sc") administration, or the implantation of a slow-release device e.g., a mini-osmotic pump, a depot formulation, and so forth, to a subject. Administration can be by any route including parenteral and transmucosal (e.g., oral, nasal, vaginal, rectal, or transdermal). Parenteral administration includes, e.g., intravenous, intramuscular, intra-arteriole, intradermal, subcutaneous, intraperitoneal, intraventricular, ionophoretic and intracranial. Other modes of delivery include the use of liposomal formulations, intravenous infusion, transdermal patches, and so forth.

"Co-administer" and "co-administering" and variants thereof refer to administration of two active agents proximate in time to one another (e.g., within the same day, or week or period of 30 days, or sufficiently proximate that both drugs can be simultaneously detected in the blood, or otherwise sufficiently proximate that a synergistic effect results from the combined administration). An effect is considered synergistic if a more favorable response and/or fewer side effects are obtained from the co-administration of two (or more) agents than from administration of the same dose of each individual agent as the dose of the combined agent (dose can be measured as moles, moles/kg, mg or mg/kg). For example, co-administration of active agents A and B is considered synergistic if co-administration of 0.5× moles A and 0.5× moles B gives a better efficacy and/or reduced side effects than the separate administration of 1.0× moles A and the separate administration of 1.0× moles B. When co-administered, two or more active agents can be co-formulated as part of the same composition or administered as separate formulations.

A "candidate agent" refers to any molecule of any composition, including proteins, peptides, nucleic acids, lipids, carbohydrates, organic molecules, inorganic molecules, and/ or combinations of molecules which are suspected to be capable of inhibiting a measured parameter in a treated cell, tissue or subject, e.g., in comparison to an untreated cell, tissue or subject. Likewise any agent determined in a screening assay or otherwise known to have such an activity is referred to as an "active agent" notwithstanding that further preclinical or clinical testing may be needed to show or confirm therapeutic activity. Active agents are sometimes referred to simply as agents or compounds.

"Metabolic syndrome" is a term of art used to describe a disorder comprising combinations of type 2 diabetes, glucose tolerance, impaired insulin sensitivity, hypertension, obesity, increased abdominal girth, hypertriglyceridemia, low HDL, hyperuricaemia, hypercoagulability and/or microalbuminemia. The International Diabetes Federation consensus worldwide definition of the metabolic syndrome (2006) is: Central obesity AND any two of the following: raised triglycerides: >150 mg/dL (1.7 mmol/L), or specific treatment for this lipid abnormality; reduced HDL cholesterol: <40 mg/dL (1.03 mmol/L) in males, <50 mg/dL (1.29 mmol/L) in females, or specific treatment for this lipid abnormality; raised blood pressure (BP): systolic BP >130 or diastolic BP >85 mm Hg, or treatment of previously diagnosed hypertension; raised fasting plasma glucose (FPG): >100 mg/dL (5.6 mmol/L), or previously diagnosed type 2 diabetes "Impaired insulin sensitivity" is a disorder in which one or more of the body's normal physiological responses to insulin are impaired or lost. Impaired insulin sensitivity in a subject is characterized by a reduced biological response to endogenous or exogenous insulin. Impaired insulin sensitivity is associated with a number of diseases or disorders in humans, including increased risk of developing type 2 diabetes. Impaired insulin sensitivity is also a feature of metabolic syndrome, which is a cluster of abnormalities that create risk for many of our most common medial diseases or disorders. Impaired insulin sensitivity can be determined by methods such as the oral glucose tolerance test (OGTT), IV glucose tolerance test (FSIVGTT), insulin tolerance test (ITT), insulin sensitivity test (1ST), and continuous infusion of glucose with model assessment (CIGMA), or the glucose clamp. See, e.g., Krentz, Insulin Resistance (Wiley-Blackwell, 2002); de Paula Martins et al., Eur. J. Obst. Gynecol. Reprod. Biol., 133 (2):203-207. Obesity, Body Mass Index (BMI) and Visceral Adiposity.

"Diabetes" is a disorder generally characterized by metabolic defects in production and utilization of glucose that result in the failure to maintain appropriate blood sugar levels in the body. The result of these defects is elevated blood glucose, referred to as "hyperglycemia." Diabetes can be defined as a disorder corresponding to a fasting plasma glucose concentration greater than or equal to 126 mg/dl (6.9 mmol/l), or a plasma glucose concentration greater than or equal to 200 mg/dl (11.1 mmol/l) two hours after ingestion of a 75 g oral glucose load. Two major forms of diabetes are type 1 diabetes and type 2 diabetes. Type 1 diabetes is generally the result of an absolute deficiency of insulin, the hormone that regulates glucose utilization. Type 2 diabetes often occurs in the face of normal, or even elevated levels of insulin and can result from the inability of tissues to respond appropriately to insulin. Most Type 2 diabetic patients are insulin resistant (i.e., having impaired insulin sensitivity) and have a relative deficiency of insulin, in that insulin secretion cannot compensate for the resistance of peripheral tissues to respond to insulin. In addition, many type 2 diabetics are obese. Type 1.5 diabetes (late autoimmune onset in adults) shows some characteristics of type 1 and type 2 diabetes.

"Obese" and "obesity" are defined according to the World Health Organization, as a Body Mass Index ("BMI") greater than 27.8 kg/m for men and 27.3 kg/m² for women (BMI equals weight (kg)/height (m²)). Obesity is linked to a variety of medical diseases or disorders including diabetes II and hyperlipidemia. (see, e.g., Barrett-Conner E, Epidemol. Rev. (1989) 11: 172-181; and Knowler, et al., Am. J. Clin. Nutr. (1991) 53: 1543-1551).

"Abdominal obesity" is a cutoff point of waist circumference >102 cm in men and >80 cm in women, as recommended by the third report of the national cholesterol education program expert panel on detection, evaluation, and treatment of high blood cholesterol in adults (NCEP/ATP Panel III).

"Glucose tolerance" refers to a state of proper functioning of the homeostatic mechanisms by which insulin is secreted in response to an elevation in serum glucose concentrations. Impairment in this system results in transient hyperglycemia as the organism is unable to maintain normoglycemia following a glucose load (for example, a carbohydrate containing meal) because of insufficient secretion of insulin from the islet beta-cells or because of insensitivity of target tissues to circulating insulin. "Impaired glucose tolerance" can be defined as a plasma glucose concentration greater than or equal to 140 mg/dl (7.8 mmol/l) two hours after ingestion of a 75 g oral glucose load.

"Body mass index" (BMI) is s a measure of body fat. The BMI of an individual is derived in a two-step mathematical formula. The individual's weight in pounds is first multiplied by 703. The product of the first step is then divided by the square of the individual's height in inches. In a metric version, BMI is calculated as the individual's weight in kilograms divided by the square of their height in meters. BMI is a frequently used medical standard to evaluate overweight and obesity.

"Hyperglycemia" refers to an above-normal level of glucose in the blood, where a normal level is in the range of from about 65 mg/dL to about 140 mg/dL. Generally, hyperglycemia refers to a blood glucose level in excess of about 140 mg/dL.

"Dyslipidemia" refers to a disorder of lipoprotein metabolism, including lipoprotein overproduction or deficiency. Dyslipidemias may be manifested by elevation of the total cholesterol, the "bad" low-density lipoprotein (LDL) cholesterol and the triglyceride concentrations, and a decrease in the "good" high-density lipoprotein (HDL) cholesterol concentration in the blood. In adult subjects dyslipidemia/hyperlipidemia is indicated when LDL cholesterol levels are more than 100 mg/dL (2.60 mmol/L), HDL cholesterol levels are equal to or lower than 40 mg/dL (1.02 mmol/L), and triglyceride levels are more than 150 mg/dL (1.7 mmol/L).

"Microalbuminuria" refers to the presence of albumin in the urine, excreted at a rate of about 20 to 200 µg/min or at a level of about 30 to 300 mg/L in humans (see, for example, Abbott, K. C., et al., Arch. Internal Med. 154: 146-153, 1994). When defined by the urinary ACR, "microalbuminuria" refers to a urinary ACR of greater than about 30 mg/g, or a urinary ACR of about 3.5 mg/mmol or greater for women and about 2.5 mg/mmol or greater for men. Methods to detect and diagnosis microalbuminuria include radioimmunoassays, immunoassays with latex bodies, fluoroimmunoassays, enzyme immunoassays, agglutination inhibition, immunoturbidimetry, immunonephelometry and radial immunodiffusion assays. (Keen, H. et al., Lancet 2: 913-916, 1968; Silver, A. et al., Clin. Chem 32: 1303-1306, 1986; Close, C. et al., Diabet. Med. 4: 491-492, 1987; Harmoinen, A. et al., Clin. Chim. Acta 166: 85-89, 1987; Mane, M. et al., Clin. Chem. 33: 209-213, 1987; McCormik, C. P. et al., Ann. Clin. Lab Sci. 19: 944-951, 1989; Cambiaso, C. L. et al., Clin. Chem. 34: 416-418, 1988; Niwa, T. et al., Clin. Chim. Acta 186: 391-396, 1990).

"Aging" refers to post-maturational processes that lead to diminished homeostasis and increased vulnerability of the organism (see Troen B. R., Mount Sinai J Med 70:3-22, 2003). Chronologic age is age from birth determined only from passage of time. Biological age is a measure of physical and mental health. An individual is assigned a biological age equal to the chronological age of a population of individuals showing a similar overall profile of physical and mental health as the individual in question. The biological age of an individual can be higher or lower than the chronological age of the individual. A lower biological age is an indicator that the individual is aging more slowly than normal and a higher biological age is an indicator that the individual is aging more rapidly than normal. Biological age can be assessed by a questionnaire asking questions regarding body mass index, general health, (e.g., digestion, cardiovascular and immune system), outlook on life, mental health, toxic load based on your diet, smoking, alcohol and the environment in which you live, and lifestyle including relationships, exercise and sexual habits. Resistance to insulin and obesity are both factors contributing to premature aging.

An "antagonist" is a molecule which, when bound to a target protein (such as Shc), decreases the amount (expression) or the duration of the effect of the biological or immunological activity of the target protein. Antagonists can be small molecules, proteins, nucleic acids, carbohydrates, or antibodies that decrease the amount (expression) or effect of the target protein present in the sample.

Subject at risk of a disease or disorder means subjects who by virtue of a known characteristic, such as a genetic marker, biomarker, or family history, are at significantly higher risk ($p \leq 0.05$) than a control population of individuals not known to have such genetic marker, biomarker or family history or the like of developing the disease or disorder.

BRIEF DESCRIPTION OF THE FIGURES

FIG. 1 illustrates that ShcKO mice have increased longevity on high fat diets (HFD).

FIGS. 2A-G illustrate that Shc depletion sensitizes the Akt arm of the insulin/IGF-1 receptor pathway.

FIGS. 3A-E illustrate that Shc KO mice have decreased white adipose in multiple fat pads, and ShcKO mice have decreased weight on high-fat diets, and ShcKO mice have increased brown fat.

FIGS. 4A-C illustrate a high-throughput screen for insulin-sensitizers based on insulin-dependent activation of Akt kinase, without activation of Erk kinase.

FIG. 5A illustrates the results of further screening of candidate drugs for their ability to stimulate phospho-Akt vs. phospho-Erk pathways (i.e. anti-Shc activity), and for the ability to modify mitochondrial bioenergetics, and scored by an objective formula. FIG. 5B illustrates the interaction of Shcs, mitochondria and insulin signaling. We observe that a large number of insulin sensitizers modify some aspect of mitochondrial bioenergetics. In FIG. 5C, 16 of 20 insulin sensitizers stimulated mitochondrial AMPK kinase, and the remaining 4 were positive in either mitochondrial $O_2$ consumption or mitochondrial ATP synthesis rate assays.

FIGS. 6A-E illustrates that Src I-1 inhibited Shc activation, and stimulated insulin sensitivity in vitro and in vivo.

FIGS. 7A-E illustrates that idebenone inhibited Shc activation, and stimulated insulin sensitivity in vitro and in vivo.

DETAILED DESCRIPTION

1. Introduction

The invention provides a new use for several existing agents, that is, for treating impaired insulin sensitivity, glucose tolerance, obesity, diabetes, aging, metabolic syndrome, or other metabolic syndrome component diseases. The new use is based in part on the finding that stimulation of phospho-Akt pathway and suppression of phospho-Erk pathway in mice results in increased glucose tolerance and insulin-sensitivity, increased glucagon, and increased glucagon-dependent hormone-sensitive lipase activation, decreased adipose in multiple fat pads, improved health characteristics on high-fat diets, improved weight, normoglycemia on high-fat diets, and increased survival on high fat diets.

Existing agents effective for the use include sulfisoxazole acetyl, metformin hydrochloride, pyronaridine tetraphosphate, azaperone, idebenone, acarbose, pefloxacine, candesartan cilexetil, cypermethrin, tripelennamine citrate, diperodon hydrochloride, aniracetam, fpa 124, methacycline hydrochloride, arctigenin, 10a, pyrithyldione, TBB, ornithine, 11e, 14e, Src I-1, BI 78D3, nitazoxanide, N-Acetyl-O-phosphono-Tyr-Glu-Glu-Ile-Glu, or a pharmaceutically acceptable salt thereof. These agents stimulate phospho-Akt over phospho-Erk relative to a control, stimulate AMP kinase activity, and perturb mitochondrial bioenergetics, without increased cytotoxicity. Some of these agents are an antagonist of the Shc protein activity or expression.

The present invention further provides an assay for screening for agents useful to treat or effect prophylaxis of one or more symptoms of impaired insulin sensitivity, glucose tolerance, obesity, diabetes, aging, metabolic syndrome, or other metabolic syndrome component diseases.

2. Subjects Amenable to Treatment

Patients amenable to treatment include individuals at risk of disease but not showing symptoms, as well as patients presently showing symptoms of impaired insulin sensitivity, glucose tolerance, obesity, diabetes, aging, metabolic syndrome, or other metabolic syndrome component diseases. For example, the subject can be presently exhibiting symptoms of impaired insulin sensitivity, glucose tolerance, obesity, diabetes, aging, metabolic syndrome, or other metabolic syndrome component diseases. For example, the subject can have a body mass index of at least 30, or have body weight 30% or more above what is considered normal.

The present methods are useful for individuals who have a known genetic risk of impaired insulin sensitivity, glucose tolerance, obesity, diabetes, aging, metabolic syndrome, or other metabolic syndrome component diseases, whether they are asymptomatic or showing symptoms of disease. For example, the subject can be asymptomatic but has familial and/or genetic risk factors for developing impaired insulin sensitivity, glucose tolerance, obesity, diabetes, aging, metabolic syndrome, or other metabolic syndrome component diseases. Such individuals include those having relatives who have experienced this disease (e.g., a parent, a grandparent, a sibling), and those whose risk is determined by analysis of genetic and/or biochemical markers. For example, such individuals include those having normal insulin sensitivity and blood glucose but a family history of diabetes or a genetic predisposition to obesity.

Genetic markers of risk toward impaired insulin sensitivity, glucose tolerance, obesity, diabetes, aging, metabolic syndrome, or other metabolic syndrome component diseases are well-known. For example, genes that have been implicated in predisposition to obesity include UCP1 and UCP2 (whose gene products regulate body temperature), LEP (whose gene product, leptin, acts on the hypothalamus to reduce appetite and increase the body's metabolism), LEPR (leptin receptor), PCSK1 (whose gene product, proprotein convertase subtilisin/kexin type 1, processes hormone precursors such as POMC), POMC (whose gene product, among other functions, stimulates adrenal glands), MC4R (whose gene product is a melanocortin 4 receptor) and Insig2 (whose gene product regulates fatty acid and cholesterol synthesis).

Other genes, which have been associated or linked with human obesity phenotypes now number above 200. Obesity gene map databases are available on the worldwide web and genes and gene maps are described in the scientific literature (see, e.g., Perusse et al., Obesity Res. 13:381-490, 2005). Any of these factors can be taken into consideration when determining a subject's risk of obesity.

Some genes implicated in developing type 2 diabetes encode the sulfonylurea receptor (ABCC8), the calpain 10 enzyme (CAPN10), the glucagon receptor (GCGR), the enzyme glucokinase (GCK), the glucose transporter (GLUT2), the transcription factor HNF4A, the insulin hormone (INS), the insulin receptor (INSR), the potassium channel KCNJ11, the enzyme lipoprotein lipase (LPL), the transcription factor PPAR gamma, the regulatory subunit of phosphorylating enzyme (PIK3R1) and others. These genes can be evaluated when identifying a subject who may benefit from the present methods. About 18 regions of the genome have been linked with type 1 diabetes risk (see, e.g., Dean et al., "The Genetic Landscape of Diabetes," National Center for Biotechnology Information (NCBI)). These regions, each of which may contain several genes, have been labeled IDDM1 to IDDM18. The most well-studied is IDDM1, which contains the HLA genes that encode immune response proteins. There are two other non-HLA genes which have been identified thus far. One, IDDM2, is the insulin gene, and the other maps close to CTLA4, which has a regulatory role in the immune response.

The present methods are also useful in suppressing the negative sequelae associated with impaired insulin sensitivity, glucose tolerance, obesity, diabetes, aging, metabolic syndrome, or other metabolic syndrome component diseases. Accordingly, patients amenable to treatment include individuals having one or more of these negative sequelae, including atherosclerosis, angina, claudication, heart attack, stroke, congestive heart failure, myocardial infarction, sleep apnea, and arthritis, vascular degeneration, macrophage proliferation and hyperactivity, plaque formation, hyperglycemia, hyper fatty acidemia, increased tumor necrosis factor and resistin levels, hypoadiponectinemia, hyper or hypo insulinemia, impaired thiol redox status (hypo-glutathione and cysteine-emia), PPARγ inactivity, and mitochondrial energy uncoupling with elevated $H_2O_2$, OHOO., cytoplasmic cytochrome c, high blood pressure, high blood cholesterol, dyslipidemia, hyperlipidemia, dyslipidemia, atherosclerotic disease including stroke, coronary artery disease or myocardial infarction, hyperinsulinemia and/or hyperproinsulinemia, microalbuminuria, delayed insulin release, diabetic complications, including coronary heart disease, angina pectoris, congestive heart failure, stroke, cognitive functions in dementia, retinopathy, peripheral neuropathy, nephropathy, glomerulonephritis, glomerulosclerosis, nephrotic syndrome, hypertensive enephrosclerosis, some types of cancer (such as endometrial, breast, prostate, and colon), complications of pregnancy, poor female reproductive health (such as menstrual irregularities, infertility, irregular ovulation, polycystic ovarian syndrome (PCOS)), lipodystrophy, cholesterol related disorders, such as gallstones, cholecystitis and cholelithiasis, gout, obstructive sleep apnea and respiratory problems, osteoarthritis, and prevention and treatment of bone loss, e.g. osteoporosis.

Patients amenable to treatment include also individuals undergoing premature aging (e.g., biological age greater than chronological age), or even individuals undergoing normal aging (biological age equal to chronological age) with a view to slowing the aging process.

Some subjects are free of a disease or disorder treatable with the active agent other than the diseases or disorders disclosed herein (e.g., diabetes, obesity, metabolic syndrome and its components, or premature aging).

Active Agents

Active agents that find use in the present methods are effective in preventing, reducing, delaying or inhibiting one or more symptoms of impaired insulin sensitivity, glucose tolerance, obesity, diabetes, aging, metabolic syndrome, or other metabolic syndrome component diseases. For example, agents increase ratio of levels of phospho-Akt-1 over phospho-ERK relative to a control ratio; increase oxygen consumption and proton production rates of cells relative to a control; increase mitochondrial $O_2$ uptake and mitochondrial oxidation of lipid; activates AMP kinase phosphorylation, in the cells of a subject with impaired insulin sensitivity, glucose tolerance, obesity, diabetes, aging, metabolic syndrome, or other metabolic syndrome component diseases. Preferably, the agents do not disrupt the cytoskeleton or microtubules in a cell.

Preferred agents include sulfisoxazole acetyl (Sigma catalog No: S6377), metformin hydrochloride (Sigma catalog No: PHR1084), pyronaridine tetraphosphate (Santa Cruz catalog No: sc-205828A), azaperone (Sigma catalog No: 34223), idebenone (Sigma catalog No: 15659), acarbose (Sigma catalog No: A8980), pefloxacine (Sigma catalog No: P0106), candesartan cilexetil (Axxora catalog No: LKT-Co254), cypermethrin (Sigma catalog No: 36128), tripelennamine citrate (Sigma catalog No: T7511), diperodon hydrochloride (Sigma catalog No: D8536), aniracetam (Sigma catalog No: A9950), fpa 124

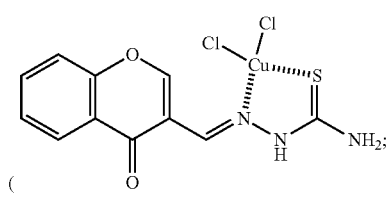

Tocris bioscience catalog No: 2926), methacycline hydrochloride (Sigma catalog No: 37906), arctigenin

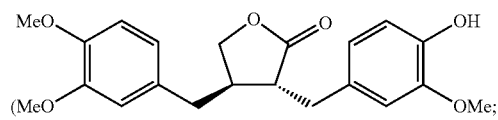

Tocris bioscience catalog No: 1777), 10a (from J. Med. Chem 2000 43:236-249, Table 2), pyrithyldione (Sigma catalog No: R279072), TBB

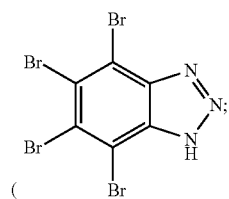

Tocris bioscience catalog No: 2275), ornithine (Sigma catalog No: O2375), 11e (from J. Med. Chem 2000 43:236-249, Table 2), 14e (from J. Med. Chem 2000 43:236-249, Table 2), Src I-1

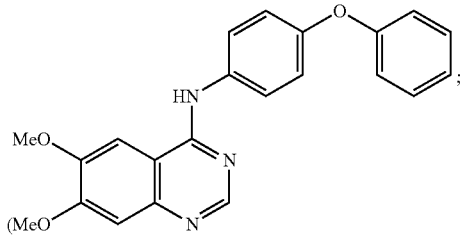

Tocris bioscience catalog No: 3642), BI 78D3

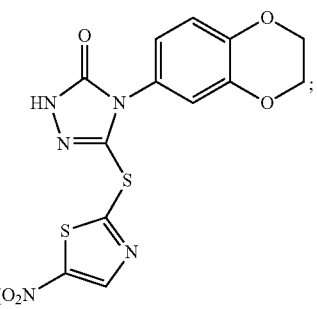

Tocris bioscience catalog No: 3314), nitazoxanide (Sigma catalog No: N0290), N-Acetyl-O-phosphono-Tyr-Glu-Glu-Ile-Glu (Tocris catalog No: 1927), or a pharmaceutically acceptable salt thereof having similar activity including ability to cross the blood brain barrier in sufficient amount to exert a therapeutic or prophylactic effect.

Other active agents are antagonists of Shc protein (as is the case for Src I-1). Such agents can be identified, for example, by performing screening methods described below. Agents can be used individually or in any combination.

3. Methods of Treatment and Prophylaxis

The subject may already exhibit symptoms of disease or be diagnosed as having impaired insulin sensitivity, glucose tolerance, obesity, diabetes, aging, metabolic syndrome, or other metabolic syndrome component disease. In such subjects, administration of one or more active agents described herein and/or analogs and/or pharmaceutically acceptable salts thereof can reverse or delay progression of and or reduce the severity of disease symptoms.

The effectiveness of treatment can be determined by comparing a baseline measure of a parameter of disease before administration of the one or more active agents described herein and/or analogs and/or pharmaceutically acceptable salts thereof is commenced to the same parameter one or more timepoints after the one or more active agents described herein and/or analogs and/or pharmaceutically acceptable salts thereof has been administered. The parameter of disease can be one or more of the signs or symptoms of impaired insulin sensitivity, glucose tolerance, obesity, diabetes, aging, metabolic syndrome, or other metabolic syndrome component diseases described herein. Measurement of a level of various biomarkers described herein in response to treatment can indicate that treatment is effective.

For the purposes of prophylaxis, the subject may be asymptomatic, but have one or more risk factors (genetic or non-genetic) described herein. For example, subjects may be asymptomatic but judged to be at high risk based on genetic tests, or other predictive tests. Alternatively, the subject may be exhibiting symptoms of early stages of a disease. In such subjects, administration of one or more active agents described herein and/or analogs and/or pharmaceutically acceptable salts thereof can prevent or delay onset or progression of diseases into later stages of diseases, and/or reduce the severity of the disease once present.

Measurable parameters for evaluating the effectiveness of the prevention regime are as discussed herein for therapy and monitoring.

4. Formulation and Administration of Active Agents a. Formulation

The one or more active agents described herein and/or analogs and/or pharmaceutically acceptable salts thereof can be administered orally, parenterally, (intravenously (IV), intramuscularly (IM), depo-IM, subcutaneously (SQ), and depo-SQ), sublingually, intranasally (e.g., inhalation, nasal mist or drops), intrathecally, topically, transmucosally, bucally, sublingually, ionophoretically or rectally.

Compositions are provided that contain therapeutically effective amounts of the one or more active agents. The compounds are preferably formulated into suitable pharmaceutical preparations such as tablets, capsules, or elixirs for oral administration or in sterile solutions or suspensions for parenteral administration.

The one or more active agents described herein and/or analogs and/or pharmaceutically acceptable salts thereof can be administered in the "native" form or, if desired, in the form of salts, esters, amides, prodrugs, derivatives, and the like, provided the salt, ester, amide, prodrug or derivative is suitable pharmacologically, i.e., effective in the present method(s). Salts, esters, amides, prodrugs and other derivatives of the active agents can be prepared using standard procedures described, for example, by March (1992) Advanced Organic Chemistry; Reactions, Mechanisms and Structure, 4th Ed. N.Y. Wiley-Interscience. Prodrugs of the agents readily undergo chemical changes under physiological conditions to provide the agents of the present invention. Conversion usually occurs after administration to a patient.

Such derivatives can be formulated by conventional methods. For example, the disulfide salts of a number of delivery agents are described in WO 2000/059863 which is incorporated herein by reference. Similarly, acid salts of agents can be prepared from the free base using conventional methodology that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent. Suitable acids for preparing acid addition salts include to both organic acids, e.g., acetic acid, carboxylic acid, propionic acid, glycolic acid, pyruvic acid, oxalic acid, malic acid, malonic acid, succinic acid, suberic acid, lactic acid, benzene sulfonic acid, p-tolylsulfonic acid, arginine, glucuronic acid, galactunoric acid phthalic acid, maleic acid, fumaric acid, tartaric acid, citric acid, benzoic acid, cinnamic acid isobutyric, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like (see, e.g., Berge et al., J. Pharm. Sci. 66, 1-19 (1977).

Although some agents have usually been supplied in the form of an HCl salt, acid salts with weaker acids (e.g., pKa 1-6-9 or preferably pKa 4-6.5) are preferred for parenteral administration. An acid addition salt can be reconverted to the free base by treatment with a suitable base. Preferred acid addition salts include halide salts, such as may be prepared using hydrochloric or hydrobromic acids. Basic salts of the active agents of this invention are prepared in a similar manner using a pharmaceutically acceptable base such as sodium hydroxide, potassium hydroxide, ammonium hydroxide, calcium hydroxide, trimethylamine, or the like. For example, basic salts can include alkali metal salts, e.g., the sodium salt, and copper salts.

For the preparation of salt forms of basic drugs, the pKa of the counterion is preferably at least about 2 pH lower than the pKa of the drug. Similarly, for the preparation of salt forms of acidic drugs, the pKa of the counterion is preferably at least about 2 pH higher than the pKa of the drug. This permits the counterion to bring the solution's pH to a level lower than the pHmax to reach the salt plateau, at which the solubility of salt prevails over the solubility of free acid or base. The generalized rule of difference in pKa units of the ionizable group in the active pharmaceutical ingredient (API) and in the acid or base is meant to make the proton transfer energetically favorable. When the pKa of the API and counterion are not significantly different, a solid complex may form but may rapidly disproportionate (i.e., break down into the individual entities of drug and counterion) in an aqueous environment.

Preferably, the counterion is a pharmaceutically acceptable counterion. Suitable anionic salt forms include acetate, benzoate, besylate, benzylate, bitartrate, bromide, carbonate, chloride, citrate, edetate, edisylate, estolate, fumarate, gluceptate, gluconate, hydrobromide, hydrochloride, iodide, lactate, lactobionate, malate, maleate, mandelate, mesylate, methyl bromide, methyl sulfate, mucate, napsylate, nitrate, pamoate (embonate), phosphate and diphosphate, salicylate and disalicylate, stearate, succinate, sulfate, tartrate, tosylate, triethiodide, valerate, and the like. Suitable cationic salt forms include aluminum, benzathine, calcium, ethylene diamine, lysine, magnesium, meglumine, potassium, procaine, sodium, tromethamine, zinc, and the like.

Preparation of esters can typically involve functionalization of hydroxyl and/or carboxyl groups that are present within the molecular structure of the active agent. For example, the esters are typically acyl-substituted derivatives of free alcohol groups, i.e., moieties that are derived from carboxylic acids of the formula RCOOH where R is alkyl, and preferably is lower alkyl. Esters can be reconverted to the free acids, if desired, by using conventional hydrogenolysis or hydrolysis procedures.

Amides can also be prepared using techniques described in the pertinent literature. For example, amides may be prepared from esters, using suitable amine reactants, or they may be prepared from an anhydride or an acid chloride by reaction with ammonia or a lower alkyl amine.

About 1 to 1000 mg of a compound or mixture of the one or more active agents or a physiologically acceptable salt or ester is compounded with a physiologically acceptable vehicle, carrier, excipient, binder, preservative, stabilizer, flavor, and so forth, in a unit dosage form as called for by accepted pharmaceutical practice. The amount of active substance in those compositions or preparations is such that a suitable dosage in the range indicated is obtained. The compositions are preferably formulated in a unit dosage form, each dosage containing from about 1-1000 mg, 2-800 mg, 5-500 mg, 10-400 mg, 50-200 mg, e.g., about 5 mg, 10 mg, 15 mg, 20 mg, 25 mg, 30 mg, 35 mg, 40 mg, 45 mg, 50 mg, 60 mg, 70 mg, 80 mg, 90 mg, 100 mg, 200 mg, 300 mg, 400 mg, 500 mg, 600 mg, 700 mg, 800 mg, 900 mg or 1000 mg of the active ingredient. The term "unit dosage from" refers to physically discrete units suitable as unitary (i.e., single) dosages for human subjects and other mammals, each unit containing a predetermined quantity of active material calculated to produce the desired therapeutic effect, in association with a suitable pharmaceutical excipient.

To prepare compositions, the one or more active agents is mixed with a suitable pharmaceutically acceptable carrier. Upon mixing or addition of the compound(s), the resulting mixture may be a solution, suspension, emulsion, or the like. Liposomal suspensions may also be suitable as pharmaceutically acceptable carriers. The form of the resulting mixture depends upon a number of factors, including the intended mode of administration and the solubility of the compound in the selected carrier or vehicle. The effective concentration is sufficient for lessening or ameliorating at least one symptom of the disease or disorder may be empirically determined.

Pharmaceutical carriers or vehicles suitable for administration of the compounds provided herein include any such carriers known to be suitable for the particular mode of administration. In addition, the active materials can also be mixed with other active materials that do not impair the desired action, or with materials that supplement the desired action, or have another action. The compounds may be formulated as the sole pharmaceutically active ingredient in the composition or may be combined with other active ingredients.

Where the compounds exhibit insufficient solubility, methods for solubilizing may be used. Such methods include, using cosolvents such as dimethylsulfoxide (DMSO), using surfactants such as Tween™, and dissolution in aqueous sodium bicarbonate. Derivatives of the compounds, such as salts or prodrugs may also be used in formulating effective pharmaceutical compositions.

The concentration of the one or more active agents is effective for delivery of an amount upon administration that lessens or ameliorates at least one symptom of the disorder for which the compound is administered and/or that is effective in a prophylactic context. Typically, the compositions are formulated for single dosage (e.g., daily) administration.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo model systems for the treated disorder. A therapeutically or prophylactically effective dose can be determined by first administering a low dose, and then incrementally increasing until a dose is reached that achieves the desired effect with minimal or no undesired side effects.

One or more active agents described herein and/or analogs and/or pharmaceutically acceptable salts thereof can be enclosed in multiple or single dose containers. The enclosed compounds and compositions can be provided in kits, for example, including component parts that can be assembled for use. For example, an agent in lyophilized form and a suitable diluent may be provided as separated components for combination prior to use. A kit may include an agent and a second therapeutic agent for co-administration. The agent and the second therapeutic agent may be provided as separate component parts. A kit may include a plurality of containers, each container holding one or more unit dose of the one or more active agents. The containers are preferably adapted for the desired mode of administration, including to tablets, gel capsules, sustained-release capsules, and the like for oral administration; depot products, pre-filled syringes, ampules, vials, and the like for parenteral administration; and patches, medipads, creams, and the like for topical or transdermal administration.

The concentration and/or amount of active compound in the drug composition depend on absorption, inactivation, and excretion rates of the active compound, the dosage schedule, and amount administered as well as other factors.

The active ingredient may be administered at once, or may be divided into a number of smaller doses to be administered at intervals of time. The precise dosage and duration of treatment is a function of the disease being treated and may be determined empirically using known testing protocols or by extrapolation from in vivo or in vitro test data. Concentrations and dosage values may also vary with the severity of the disease or disorder to be alleviated. For any particular subject, specific dosage regimens can be adjusted over time according to the individual need and the professional judgment of the person administering or supervising the administration of the compositions, and that the concentration ranges set forth herein are exemplary only and are not intended to limit the scope or practice of the claimed compositions.

If oral administration is desired, the compound can be provided in a formulation that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions generally include an inert diluent or an edible carrier and may be compressed into tablets or enclosed in gelatin capsules. For the purpose of oral therapeutic administration, the active compound or compounds can be incorporated with excipients and used in the form of tablets, capsules, or troches. Pharmaceutically compatible binding agents and adjuvant materials can be included as part of the composition.

The tablets, pills, capsules, troches, and the like can contain any of the following ingredients or compounds of a similar nature: a binder such as, gum tragacanth, acacia, corn starch, or gelatin; an excipient such as microcrystalline cellulose, starch, or lactose; a disintegrating agent such as, alginic acid and corn starch; a lubricant such as magnesium stearate; a gildant, such as, colloidal silicon dioxide; a sweetening agent such as sucrose or saccharin; and a flavoring agent such as peppermint, methyl salicylate, or fruit flavoring.

When the dosage unit form is a capsule, it can contain, in addition to material of the above type, a liquid carrier such as a fatty oil. In addition, dosage unit forms can contain various other materials, which modify the physical form of the dosage unit, for example, coatings of sugar and other enteric agents. The compounds can also be administered as a component of an elixir, suspension, syrup, wafer, medicated chewing gum or the like. A syrup may contain, in addition to the active compounds, sucrose as a sweetening agent and certain preservatives, dyes and colorings, and flavors.

The active materials can also be mixed with other active materials that do not impair the desired action, or with materials that supplement the desired action.

Solutions or suspensions used for parenteral, intradermal, subcutaneous, or topical application can include any of the following components: a sterile diluent such as water for injection, saline solution, fixed oil, a naturally occurring vegetable oil such as sesame oil, coconut oil, peanut oil, cottonseed oil, and the like, or a synthetic fatty vehicle such as ethyl oleate, and the like, polyethylene glycol, glycerine, propylene glycol, or other synthetic solvent; antimicrobial agents such as benzyl alcohol and methyl parabens; antioxidants such as ascorbic acid and sodium bisulfite; chelating agents such as ethylenediaminetetraacetic acid (EDTA); buffers such as acetates, citrates, and phosphates; and agents for the adjustment of tonicity such as sodium chloride and dextrose. Parenteral preparations can be enclosed in ampoules, disposable syringes, or multiple dose vials made of glass, plastic, or other suitable material. Buffers, preservatives, antioxidants, and the like can be incorporated as required.

Suitable carriers for intravenous administration include physiological saline, phosphate buffered saline (PBS), and solutions containing thickening and solubilizing agents such as glucose, polyethylene glycol, polypropyleneglycol, and mixtures thereof. Liposomal suspensions including tissue-targeted liposomes may also be suitable as pharmaceutically acceptable carriers. These may be prepared according to methods known for example, as described in U.S. Pat. No. 4,522,811.

The one or more active agents described herein and/or analogs and/or pharmaceutically acceptable salts thereof may be prepared with carriers that protect them against rapid elimination from the body, such as time-release formulations or coatings. Controlled release is a mechanism of formulation to release a drug over an extended time. Use of controlled release formulation may reduce the frequency of administration, reduce fluctuations in blood concentration and protect the gastrointestinal tract from side effects. The active compounds may be prepared with carriers that protect the compound against rapid elimination from the body, such as time-release formulations or coating. Such carriers include controlled release formulations (also known as modified, delayed, extended or sustained release or gastric retention dosage forms, such as the Depomed GR™ system in which agents are encapsulated by polymers that swell in the stomach and are retained for about eight hours, sufficient for daily dosing of many drugs). Controlled release systems include microencapsulated delivery systems, implants and biodegradable, biocompatible polymers such as collagen, ethylene vinyl acetate, polyanhydrides, polyglycolic acid, polyorthoesters, polylactic acid, matrix controlled release devices, osmotic controlled release devices, multiparticulate controlled release devices, ion-exchange resins, enteric coatings, multilayered coatings, microspheres, liposomes, and combinations thereof. The release rate of the active ingredient can also be modified by varying the particle size of the active ingredient(s). Examples of modified release include, e.g., those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500.

b. Route of Administration and Dosing

The one or more active agents described herein and/or analogs and/or pharmaceutically acceptable salts thereof can be administered orally, parenterally (IV, IM, depo-IM, SQ, and depo-SQ), sublingually, intranasally (inhalation), intraspinally, intrathecally, topically, or rectally. Dosages of agents that are known for prior use to treat or prevent a disease or disorder other than impaired insulin sensitivity, glucose tolerance, obesity, diabetes, aging, metabolic syndrome, or other metabolic syndrome component diseases may provide a starting point for the purpose of ameliorating the symptoms of impaired insulin sensitivity, glucose tolerance, obesity, diabetes, aging, metabolic syndrome, or other metabolic syndrome component diseases.

The one or more active agents described herein and/or analogs and/or pharmaceutically acceptable salts thereof may be administered enterally or parenterally. Oral formulations include tablets and capsules as well as liquid dosage forms such as solutions, suspensions, and elixirs. When the solid dosage forms are used, it is preferred that they be of the sustained release type so that the one or more active agents need to be administered only once or twice daily (or less frequency).

The oral dosage forms can be administered to the patient 1, 2, 3, or 4 times daily or less frequently, such as on alternate days, every third day, twice a week or once a week. It is preferred that the one or more active agents be administered either three or fewer times, more preferably once or twice daily. Oral dosage forms are preferably designed so as to protect the one or more active agents from the acidic environment of the stomach, such as by enteric coated or by use of capsules filled with small spheres each coated to protect from the acidic stomach.

When administered orally, an administered amount therapeutically effective to prevent, mitigate or treat impaired insulin sensitivity, glucose tolerance, obesity, diabetes, aging, metabolic syndrome, or other metabolic syndrome component diseases is from about 0.1 mg/day to about 200 mg/day, for example, from about 1 mg/day to about 100 mg/day, for example, from about 5 mg/day to about 50 mg/day. The subject can be administered the one or more active agents at a dose of about 0.05 to about 0.50 mg/kg or 0.1 mg/kg-10 mg/kg or 0.5 mg/kg to 5 mg/kg, for example, about 0.05 mg/kg, 0.10 mg/kg, 0.20 mg/kg, 0.33 mg/kg, 0.50 mg/kg, 1 mg/kg, 5 mg/kg or 10 mg/kg. Although a patient may be started at one dose, that dose may be varied (increased or decreased, as appropriate) over time as the patient's condition changes. Depending on outcome evaluations, higher doses may be used. For example, in certain subjects, up to as much as 1000 mg/day can be administered, e.g., 200 mg/day, 300 mg/day, 400 mg/day, 500 mg/day, 600 mg/day, 700 mg/day, 800 mg/day, 900 mg/day or 1000 mg/day.

The one or more active agents described herein and/or analogs and/or pharmaceutically acceptable salts thereof may also be advantageously delivered in a nano crystal dispersion formulation (see U.S. Pat. No. 5,145,684 or U.S. Pat. No. 6,045,829). The nano crystalline formulations typically afford greater bioavailability of drug compounds.

The one or more active agents and/or analogs thereof can be administered parenterally, for example, by IV, IM, depo-IM, SC, or depo-SC. When administered parenterally, a therapeutically effective amount of about 0.5 to about 1000 mg/day, preferably from about 5 to about 500 or 50-200 mg daily should be delivered. The parenteral dosage form can be a depo formulation in which case a larger amount of drug can be administered with reduced frequency.

The one or more active agents and/or analogs thereof can be administered sublingually. When given sublingually, the one or more active agents and/or analogs thereof can be given one to four times daily in the amounts described above for IM administration.

The one or more active agents and/or analogs thereof can be administered intranasally. Appropriate formulations include a nasal spray or dry powder. The dosage of the one or more active agents and/or analogs thereof for intranasal administration is the amount described above for IM administration.

The one or more active agents and/or analogs thereof can be administered intrathecally in a parenteral formulation. The dosage of the one or more active agents and/or analogs thereof for intrathecal administration is the amount described above for IM administration.

The one or more active agents and/or analogs thereof can be administered topically or transdermally. When given by this route, the appropriate dosage form is a cream, ointment, or patch. When administered topically, the dosage can be from about 0.5 mg/day to about 200 mg/day. Because the amount that can be delivered by a patch is limited, two or more patches may be used. The number and size of the patch is not important, what is important is that a therapeutically effective amount of the one or more active agents and/or analogs thereof be delivered. The one or more active agents and/or analogs thereof can be administered rectally by suppository. When administered by suppository, the therapeutically effective amount can be from about 0.5 mg to about 500 mg.

The one or more active agents and/or analogs thereof can be administered by implants. When administering one or more active agents by implant, the therapeutically effective amount is the amount described above for depot administration.

The exact dosage and frequency of administration depends on the particular disease or disorder being treated, the severity of the disease or disorder being treated, the age, weight, general physical condition of the particular patient, and other medication the individual may be taking.

5. Combination Therapies

The one or more active agents described herein and/or analogs thereof can be used in combination with each other or with other therapeutic agents or approaches used to treat, mitigate or prevent impaired insulin sensitivity, glucose tolerance, obesity, diabetes, aging, metabolic syndrome, or other metabolic syndrome component diseases. For example, the one or more active agents described herein and/or analogs thereof can be co-administered with insulin. Insulin is frequently required in patients with long standing diabetes mellitus, and one or more active agents described herein may lower the insulin requirements. Insulin at high doses may have a proatherogenic effect. The combination drug will, therefore, have multiple benefits compared to insulin alone.

The one or more active agents described herein and/or analogs thereof can be co-administered with other diabetes drugs and obesity drugs. Diabetes drugs suitable for combination therapy include sulfonylurea agents such as glipizide, glyburide (glibenclamide), chlorpropamide, tolbutamide, tolazamide and glimepriride, or the pharmaceutically acceptable salt forms thereof (see, e.g., US 2003/008869); biguanide agents such as mefformin and its pharmaceutically acceptable salt forms (see, e.g., U.S. Patent Pub. No. 2003/0018028); thiazolidinedione agents pioglitazone or rosiglitazone, or a pharmaceutically acceptable salt form thereof (see, e.g., US 2002/0198203); alpha-glucosidase inhibitors such as miglitol or acarbose, or a pharmaceutically acceptable salt form thereof (see, e.g., US 2003/0013709); antilipemic agents (also known as antihyperlipidemic agents) such as bile acid sequestrants, fibric acid derivatives, HMG-CoA reductase inhibitors and nicotinic acid compounds (see, e.g., U.S. Patent Application No. 2002/0198202); angiotensin converting enzyme (ACE) inhibitors such as quinapril, ramipril, verapamil, captopril, diltiazem, clonidine, hydrochlorthiazide, benazepril, prazosin, fosinopril, lisinopril, atenolol, enalapril, perindropril, perindropril tert-butylamine, trandolapril and moexipril, or a pharmaceutically acceptable salt form thereof (see, e.g., U.S. Patent Application No. 2003/0055058); aldose reductase inhibitors (preventing eye and nerve damage in people with diabetes) such as minalrestat Tolrestat, Sorbinil, Methosorbinil, Zopolrestat, Epalrestat, Zenarestat Imirestat, and Ponalrestat or the pharmaceutically acceptable salt forms thereof (see, e.g., U.S. Patent Application No. 2002/0198201). Obesity drugs suitable for combination therapy include central nervous system (CNS) stimulants such as phentermines (e.g., those sold under the tradenames Ionamin® and Adipex-P®) (see, e.g., U.S. Pat. No. 5,019,594). The phentermines are members of a class of drugs known as the sympathomimetics for their ability to mimic stimulation of the central nervous system; re-uptake inhibitors such as 5HT-2C inhibitors (e.g., Meridia® (sibutramine), Lorcaserin (APD-356)) (see, e.g., U.S. Pat. No. 4,929,629); CB-1 antagonists such as rimonabant (Acomplia®) and CP-945598 (see, e.g., U.S. Pat. No. 5,624,941); and GLP-1 agonists or mimetics such as exenatide (Byetta®) (see, e.g., U.S. Pat. No. 5,424,286).

6. Insulin Signaling Pathway

Insulin action is mediated by signal transduction over the insulin receptor. The insulin receptor belongs to the superfamily of receptor tyrosine kinases and consists of 2 extracellular alpha subunits and 2 intracellular beta subunits. Insulin binding to the alpha subunit results in a conformational change, which leads to activation of the tyrosine kinase in the intracellular domain, adenosine triphosphate binding and finally receptor autophosphorylation (White, Science, 302:1710-1711, 2003).

Insulin receptor autophosphorylation is followed by phosphorylation of the insulin-receptor substrates (IRS). IRS are related by functional properties and not sequence similarity. Four substrates belong to the family of IRS, IRS-1, IRS-2, IRS-3, and IRS-4. Other substrates include growth factor receptor-bound protein 2 (GRB2)-associated binding protein 1 (Gab-1), p60dok, the c-Cbl proto-oncogene (Cbl), adaptor protein with pleckstrin homology (PH) and Src homology 2 domains (APS) and 3 isoforms of Src homology 2 (SH2) domain-containing alpha-2 collagen-related protein (Shc) (Virkamäki et al., J Clin Invest. 103:931-943, 1999). IRS contain an NH2-terminal PH domain and/or a phosphotyrosine-binding domain, COOH-terminal tyrosine residues that create SH2 protein-binding sites, prolinerich regions that engage Src homology 3 (SH3) domains or WW domains (protein modules that bind proline-rich ligands) and serine-threonine-rich regions that bind other proteins. All substrates, except Shc, contain a SH2 domain that targets the substrate to the insulin receptor (White, Science, 302:1710-1711, 2003). There are 3 main pathways that propagate the signal generated through the insulin receptor: the IRS/phosphatidylinositol 3 (PI3)-kinase pathway; the retrovirus-associated DNA sequences (RAS)/mitogen-activated protein kinase (MAPK) pathway; and the Cbl-associated protein (CAP)/Cbl pathway (FIG. 2A).

Shc is a member of the RAS/MAPK/ERK pathway (FIG. 4). Shc is an adaptor-type intracellular signaling protein containing both SH2 and PTB domains (Blaikie, J. Biol. Chem. 269:32031-32034, 1994; van der Geer, Curr. Biol. 5:404-412, 1995; Pelicci, Oncogene 13:633-641, 1996). Shc is capable of binding to phosphorylated tyrosine residues of the cytoplasmic domain of insulin receptor (by virtue of its PTB or SH2 domains), as well as to other intracellular signaling molecules, thus playing a role in the intracellular transduction of an insulin receptor-derived signal.

At the cellular level, reduction of Shc leads to decreased Ras-dependent phosphorylation and cell proliferation, and increased Akt-dependent phosphorylation and metabolism, and insulin sensitivity (FIG. 2, 4C). Shc knockdown in vitro stimulates phospho-Akt and removes inhibitory phosphorylation of mitochondrial PDH (FIG. 2E). At the organismal level, PET scanning indicates that deficiencies of Shc increased insulin-dependent glucose uptake in brown fat, muscle, and liver of Shc-reduced mice (not shown). In Shc-reduced mouse tissues insulin pathway enzymes such as phospho-Akt and phospho-IRS1 are activated (FIG. 2D). Shc-reduced mice have increased brown adipose activity (FIG. 3D) and differentiation (FIG. 3E), expression of uncoupling protein (UCP-1), increased mitochondrial uncoupling and activity (FIG. 3D), and increased lipid oxidation gene expression (not shown). In mice, Shc reduction results in increased glucose tolerance and insulin-sensitivity (FIG. 2C, 2G). Shc-reduced mice have decreased adipose in multiple fat pads (FIG. 3A), improved health characteristics on high-fat diets, improved weight (FIG. 3B), and are normoglycemic on high-fat diets (FIG. 2G). Reduction of Shc in mice results in increased survival on high fat diets (FIG. 1).

7. Monitoring Efficacy

Clinical efficacy can be monitored by measuring one or more of the disease parameters or physical symptoms of impaired insulin sensitivity, glucose tolerance, obesity, diabetes, aging, metabolic syndrome, or other metabolic syndrome component diseases, including blood pressure, blood insulin, free fatty acid, bodyweight, triglyceride levels, blood glucose levels, high body mass index. Observation of the stabilization, improvement and/or reversal of one or more symptoms indicates that the treatment or prevention regime is efficacious. Observation of the progression, increase or exacerbation of one or more symptoms indicates that the treatment or prevention regime is not efficacious.

Clinical efficacy can also be monitored using biomarkers. Biomarkers for assessing treatment are preferably assessed at the protein level, but measurement of mRNA encoding biomarkers can also be used as a surrogate measure of biomarker expression. Such a level can be measured in a blood sample, e.g., on PBMC's. The level of some biomarkers are reduced in subjects with impaired insulin sensitivity, glucose tolerance, obesity, diabetes, aging, metabolic syndrome, or other metabolic syndrome component diseases relative to a control population of undiseased individuals. An increase in level of such a marker provides an indication of a favorable treatment response, whereas an unchanged or decreasing levels provides an indication of unfavorable or at least non-optimal treatment response. The level of other biomarkers is increased in subjects with impaired insulin sensitivity, glucose tolerance, obesity, diabetes, aging, metabolic syndrome, or other metabolic syndrome component diseases relative to a control population of undiseased individuals. An decrease in level of such a biomarker provides an indication of a favorable treatment response, whereas an unchanged or increasing levels provides an indication of unfavorable or at least non-optimal treatment response.

The monitoring methods can entail determining a baseline value of a measurable biomarker or disease parameter in a subject before administering a dosage of the one or more active agents described herein, and comparing this with a value for the same measurable biomarker or parameter after a course of treatment.

In other methods, a control value (i.e., a mean and standard deviation) of the measurable biomarker or parameter is determined for a control population. A suitable control population is one in which subjects have not received prior treatment and do not have a target disease, nor are at known risk of developing a target disease. In such methods, if the value of the measurable biomarker or clinical parameter approaches the control value, then treatment is considered efficacious. In other methods, the individuals in the control population have not received prior treatment and have been diagnosed with a target disease. In such methods, if the value of the measurable biomarker or clinical parameter approaches the control value, then treatment is considered inefficacious.

In other methods, a subject who is not presently receiving treatment but has undergone a previous course of treatment is monitored for one or more of the biomarkers or clinical parameters to determine whether a resumption of treatment is required. The measured value of one or more of the biomarkers or clinical parameters in the subject can be compared with a value previously achieved in the subject after a previous course of treatment. Alternatively, the value measured in the subject can be compared with a control value (mean plus standard deviation or preferably two standard deviations) determined in population of subjects after undergoing a course of treatment. Alternatively, the measured value in the subject can be compared with a control value in populations of prophylactically treated subjects who remain free of symptoms of disease, or populations of therapeutically treated subjects who show amelioration of disease characteristics. In such cases, if the value of the measurable biomarker or clinical parameter approaches the control value, then treatment is considered efficacious and need not be resumed. On the other hand, a significant difference relative to the control level (i.e., more than one or preferably two standard deviations) is an indicator that treatment should be resumed in the subject.

8. Screening for Agents

Assays to identify compounds useful for preventing, reducing, delaying or inhibiting symptoms of impaired insulin sensitivity, glucose intolerance or obesity can be performed in vitro. Candidate agents can be contacted with a population of test cells in the presence of insulin (e.g., 1 nM, 5 nM, 10 nM, 100 nM or more). An agent that prevents, reduces, delays or inhibits one or more symptoms of impaired insulin sensitivity, glucose intolerance or obesity increases the ratio of levels of phospho-Akt-1 over phospho-Erk relative to a control ratio. The increase in ratio of levels of phospho-Akt-1 over phospho-Erk can be determined in comparison to a control population of cells that have not been contacted with insulin or have been contacted with a low concentration of insulin (e.g., less than 0.1 nM) or a population of cells contacted with insulin but not with the compound under test. Ratio of levels of phospho-Akt-1 over phospho-Erk can be determined using a Western blot among other methods. Inhibition of Shc activity can be quantitatively measured by assaying the reduction of stimulatory Shc phosphorylation, using a phospho-Shc specific antibody. Inhibition of Shc expression can be measured using a Western blot.

Agents of interest can be further selected for their ability to produce drug-dependent effects on mitochondrial physiology, e.g., oxygen consumption and proton production rates of cells. Oxygen consumption and proton production rates of cells can be determined using the Seahorse machine (Seahorse Bioscience, Billerica, Mass.). Agents of interests can also be further selected for their ability to produce drug-dependent effects on mitochondrial O2 uptake. Mitochondrial O2 uptake can be determined using biosensor plates (e.g., BD™ Oxygen Biosensor systems; BD Biosciences, San Jose, Calif.). Agents of interests can also be further selected for their ability to produce drug-dependent effects on phospho-AMP kinase. Phospho-AMP kinase can be assayed using the HITHUNTER™ Kinase Toolbox (DiscoveRx, Fremont, Calif.) or as described in WO 02/09726, among other methods. Agents of interest can also be further selected based on their ability to inhibit mitochondrial ATP synthesis. Agents of interests can also be further selected based on the agents' cytotoxicity. Cytotoxicity can be determined using any known method, e.g., tubulin polymerization assay (S. Kuo et al., J. Med. Chem. 36, 1146, 1993; L. Li et al., J. Med. Chem. 37, 3400, 1994; L. Li et al., J. Med. Chem. 37, 1126, 1994; Y. Xia et al., J. Med. Chem. 41, 1155, 1998).

Agents of interest can be selected based on their ability to increase the ratio of levels of phospho-Akt-1 over phospho-Erk by for example, at least about 1.4-fold, 1.5-fold, 1.6-fold, 1.7-fold, 1.8-fold, 1.9-fold, 2.0-fold, 5.0 fold, 10.0 fold, or more, relative to a control ratio. Some agents increase the ratio within a range of X to Y fold. Agents of interest can also be selected based on their ability to increase ratio of levels of phospho-Akt-1 over phospho-Erk relative to a control ratio with a low EC50 concentration, for example, an EC50 concentration of less than about 5 $\mu$M, for example, less than about 4 $\mu$M, 3 $\mu$M, 2 $\mu$M, 1 $\mu$M, 0.5 $\mu$M or less. Active agents of interest can be further confirmed by testing their ability to increase ratio of levels of phospho-Akt-1 over phospho-Erk relative to a control ratio in a dose-dependent manner.

Drug-dependent effects and/or cytotoxicity can be determined in cells or animals models (see, e.g., Srinivasa et al., (2007) Indian J. Med. Res. 127:451-472, T. S. Frode et al. (2008), Journal of Ethnopharmacology 115:173-183 and Rees et al. (2005) Diabet Med. 22: 359-370). These include models in which diabetes mellitus is induced pharmacologically with agents such as, for example, streptozotocin or alloxan. Both alloxan and streptozotocin are toxic glucose analogues that accumulate in pancreatic beta cells via the GLUT2 glucose transporter, resulting in the inhibition of insulin secretion, and inducing hyperglycemia. Animal models in which diabetes is surgically induced are also available. For example, diabetes can be induced by surgically removing the pancreas from an animal.

Genetic animal models of obesity, insulin resistance and/or diabetes are also available. Such models are based on either strains of animals that spontaneously develop obesity, insulin resistance and/or diabetes or on rodents that are genetically susceptible or have been genetically engineered to develop obesity, insulin resistance and/or diabetes. Examples of animals that spontaneously develop obesity, insulin resistance and/or diabetes include the Zucker diabetic fatty rat, SHR/N-cp rat, JCR/LA-cp rat, Toni rat, Agouti mouse, db/db mouse, ob/ob mouse, and KKA$\gamma$ mice.

Nutritionally induced animal models of diabetes and/or insulin resistance can also be used. Examples include the high fat high sucrose rat (Tremblay et al. (2001) Diabetes 50:1901-1910), the 10% glucose rat (El Midaoui A. et al., (2002) Hypertension 39:303-307), desert rodent models (Shafrir et al. (2006) ILAR J. 47:212-224) and high fat-fed mice.

The candidate agent can be a small organic compound, a polypeptide, an antibody or fragment thereof, an amino acid or analog thereof, a carbohydrate, a saccharide or disaccharide, or a polynucleotide.

The invention provides further screening methods in which agents are initially screened to determine whether they have an antagonist effect on the Shc protein. Agents having such an effect can then be screened in a cellular or animal model of impaired insulin sensitivity, glucose tolerance, obesity, diabetes, aging, metabolic syndrome, or other metabolic syndrome component diseases to determine whether an agent has an activity providing an indication of utility in treatment of these diseases.

The screening methods of the invention can be performed in a high-throughput format. Such high throughput screening methods can involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known. Such combinatorial chemical libraries include peptide libraries (see, e.g. U.S. Pat. No. 5,010, 175, Furka, Int J Pept Prot Res 37:487-493 (1991) and Houghton, et al., Nature 354:84-88 (1991)). Other chemistries for generating chemical diversity libraries can also be used. Such chemistries include to peptoids (e.g., WO 91/19735), encoded peptides (e.g., WO 93/20242), random bio-oligomers (e.g., WO 92/00091), benzodiazepines (e.g., U.S. Pat. No. 5,288,514), diversomers such as hydantoins, benzodiazepines and dipeptides (Hobbs, et al, *Proc Nat Acad Sci USA* 90:6909-6913 (1993)), vinylogous polypeptides (Hagihara, et al., *J Amer Chem Soc* 114:6568 (1992)), nonpeptidal peptidomimetics with glucose scaffolding (Hirschmann, et al., *J Amer Chem Soc* 114:9217-9218 (1992)), analogous organic syntheses of small compound libraries (Chen, et al., *J Amer Chem Soc* 116:2661 (1994)), oligocarbamates (Cho, et al., *Science* 261:1303 (1993)) and/or peptidyl phosphonates (Campbell, et al., *J Org Chem* 59:658 (1994)), nucleic acid libraries, peptide nucleic acid libraries (see, e.g. U.S. Pat. No. 5,539,083), antibody libraries (see, e.g., Vaughn et al., *Nature Biotechnology*, 14(3): 309-314 (1996) and PCT/US96/10287), carbohydrate libraries (see, e.g., Liang, et al., *Science* 274:1520-1522 (1996) and U.S. Pat. No. 5,593,853), small organic molecule libraries (see, e.g., benzodiazepines, Baum, C&EN, January 18, page 33 (1993), isoprenoids, U.S. Pat. No. 5,569,588), thiazolidinones and metathiazanones, U.S. Pat. No. 5,549, 974 pyrrolidines, U.S. Pat. Nos. 5,525,735 and 5,519,134, morpholino compounds, U.S. Pat. No. 5,506,337 benzodiazepines, U.S. Pat. No. 5,288,514, and the like).

Devices for the preparation of combinatorial libraries are commercially available (see, e.g., 357 MPS, 390 MPS, Advanced Chem Tech. Louisville Ky.; Symphony, Rainin, Woburn, Mass.; 433A Applied Biosystems, Foster City, Calif.; 9050 Plus, Millepore, Bedford. Mass.). In addition, numerous combinatorial libraries are themselves commercially available (see, e.g., ComGenex, Princeton, N.J.; Tripos, Inc, St Louis, Mo.; 3D Pharmaceuticals, Eaton, Pa.; Martek Biosciences, Columbia, Md.). Libraries of FDA approved compounds are commercially available and find use (e.g., from Enzo Life Sciences (enzolifesciences.com); and Microsource Discovery Systems (msdiscovery.com)). Chemical libraries with candidate agents selected for bioavailability and blood-brain barrier penetration also find use, and are commercially available, e.g., from ChemBridge (chembridge.com) and Prestwick Chemical (prestwick-chemical.fr). Further libraries of chemical agents that find use are available, e.g., from Evotec (evotec.com); Magellan BioScience Group (magellanbioscience.com); and Cellumen (cellumen.com).

High throughput assays of the invention screen up to several thousand different candidate agents in a single day. In particular, each well of a microtiter plate can be used to run a separate assay against a selected potential candidate agent, or, if concentration or incubation time effects are to be observed, every 5-10 wells can test a single modulator. Thus, a single standard microtiter plate can assay about 100 (e.g., 96) candidate agents. Multiwell plates with greater numbers of wells find use, e.g., 192, 384, 768 or 1536 wells. If 1536-well plates are used, then a single plate can easily assay from about 100 to about 1500 different compounds. It is possible to assay several different plates per day. Assay screens for up to about 6,000-20,000 different compounds are possible using the integrated systems of the invention.

EXAMPLES

Example 1. ShcKO Mice have Increased Longevity on High Fat Diets (HFD)

On high-fat diets with similar mouse numbers at days of age, mean and maximal survival is higher in ShcKO mice than controls (FIG. 1).

Lifespan Measurement Protocol:

The groups of age-matched mice were started on the indicated diets at 2 month of age. The body weight, food consumption and date of death were recorded.

Example 2. Shc Depletion Sensitizes the Akt Arm of the Insulin/IGF-1 Receptor Pathway Decreased Shc activity decreases the activity of the Ras-oncogene pathway (FIG. 2A, dark asterisk), but increases the activity of the Akt-prosurvival/metabolic pathway (FIG. 2A, white asterisk). In ShcKO mice, p66Shc is deleted and, in addition, in several tissues such as muscles, liver, heart, pancreas, brown fat the p52Shc and p46Shc expression is significantly decreased (FIG. 2B). ShcKO mice have increased insulin sensitivity (FIG. 2C, top), and improved glucose tolerance (FIG. 2C, bottom). ShcKO mice (FIG. 2D) and Shc-depleted cells (FIG. 2E) have increased insulin-dependent activation of Akt (Akt phosphorylation) and IRS1, but no increase in Erk activation. As a result of reduced Shc-expression, even obese mice fed a high-fat diet maintain higher metabolic insulin-sensitivity in terms of activation of Akt (FIG. 2F), and consequently overcome HFD induced development of hyperglycemia (FIG. 2G).

Western Blot Protocol for FIG. 2B:

Total protein was isolated from mouse tissues using Cell Lysis buffer containing 20 mM Tris-HCl (pH 7.5), 150 mM NaCl, 1 mM Na2EDTA, 1 mM EGTA, 1% Triton, 2.5 mM sodium pyrophosphate, 1 mM β-glycerophosphate, 1 mM Na3VO4, 100 mM DTT, 1 µg/ml Leupeptin, 1 mM Phenylmethanesulfonyl fluoride and supplemented with Complete Mini Protease Inhibitor Cocktail and PhosStop Phosphatase Inhibitor Cocktail (Roche). Forty microgram of protein per line, as determined by Bradford assay (Bio-Rad Laboratories), were resolved by SDS-PAGE, transferred to nitrocellulose membrane, blocked with Odyssey Blocking Buffer (Li-Cor Biosciences) and hybridized with rabbit polyclonal anti-Shc antibody (BD Bioscience) and mouse monoclonal anti-Tubulin antibodies (Sigma) followed by development with goat anti-rabbit monoclonal antibody labeled with IR-dye 700 CW and goat anti-mouse monoclonal antibody labeled with IR-dye 800 CW (Li-Cor Biosciences). Blots were scanned on Licor Odyssey infrared imaging instrument and quantified using Odyssey 2.1 software. Use of different IR-dyes labeled secondary antibodies allowed to measure level of housekeeping proteins (in this particular case—tubulin) at the same time as the proteins of interest (Shc isoforms) on the same membrane at the same time, and this improves accuracy of quantification and normalization.

Insulin Tolerance Test (ITT) and Glucose Tolerance Test (GTT) Protocol for FIG. 2C:

Groups of age/sex matched mice of Control and ShcKO genotypes were food deprived for four hours and challenged with I.P. injection of insulin, and glucose concentration was determined in blood exactly at indicated time-points. Decrease and recovery of blood glucose was calculated as a % of basal level (the time-point before insulin injection). Basal levels of glucose were measured in triplicate for each mouse. For the GTT, the same groups of mice were fasted during fourteen hours and challenged with glucose injection I.P., analogously the blood glucose concentrations were measured.

Acute Tissue Insulin Sensitivity Test (ATIST) Protocol for FIG. 2D:

Mice were fasted for six hours and anesthesia was started by I.P. injection of pentobarbital 100 mg per kg of body weight. Peritoneal cavity was open and small biopsies of desired tissues were taken and frozen in liquid nitrogen. Insulin was injected through inferior vena-cava and biopsies were taken again at different precise time-points post insulin treatment. Total protein was isolated using Cell Lysis buffer (Cell Signaling Technologies), containing 20 mM Tris-HCl (pH 7.5), 150 mM NaCl, 1 mM Na2EDTA, 1 mM EGTA, 1% Triton, 2.5 mM sodium pyrophosphate, 1 mM β-glycerophosphate, 1 mM Na3VO4, 100 mM DTT, 1 µg/ml leupeptin, 1 mM Phenylmethanesulfonyl fluoride and additionally supplemented with Complete Mini Protease Inhibitor Cocktail and PhosStop Phosphatase Inhibitor Cocktail (Roshe). Forty microgram of protein per line, as determined by Bradford assay (Bio-Rad Laboratories), were resolved by SDS-PAGE, transferred to nitrocellulose membrane, blocked with Odyssey Blocking Buffer (Li-Cor Biosciences) and hybridized with indicated primary antibody followed by development with infrared IR-dye 700 CW and/or 800 CW labeled secondary antibodies (Li-Cor) as described previously. In FIG. 2D, the result of testing muscle tissue is presented, and time-points before insulin injection (insulin "−") and 300 seconds after the insulin injection (insulin "+") are presented.

ATIST Protocol for FIG. 2F:

The High Fat Diet was based on AIN-93G diet (Teklad TD.94045) and adjusted to have 60% of fat and 7.3% of carbohydrates and 17.7% protein derived calories. The primary source of lipid was soybean oil, the primary protein source was casein and the primary source of carbohydrates was corn starch. The MFD (Moderate Fat Diet) is a control AIN-93G diet (Teklad TD.94045) diet with normal fat content. The protein-derived calories were the same in the HFD and MFD. Mice were put on indicated diets at three month of age and maintained for four month. The ATIST was performed as described above. In FIG. 2F, the results of ATIST for liver is presented at time "0" (insulin "−") and 90 seconds after insulin injection (insulin "+").

Insulin Signaling Measurements In-Vitro in Cells with Silenced Shc for FIG. 2E:

HeLa cells were transfected with indicated siRNA. Transfection was carried out on 6 well plates (Nunc). Two hundred thousand cells per well were plated in antibiotic free DMEM 10% FBS and after settlement washed with PBS. Transfection mixture was prepared using 10 nM siRNA specific for Shc or non-specific AllStar siRNA (Qiagen), OPTIMEM media (Invitrogen) and Lipofectamine 2000 (Invitrogen) according to manufacturer protocol. After six hours of transfection in 600 µl of transfection mixture cells were feed with fresh DMEM. Cells were maintained on DMEM 10% FBS, 25 mM glucose for 48 hours. Total proteins were extracted and Western-analyzed with indicated antibody as described above. Phosphorylation levels of Akt (activatory phosphorylation) and PDH (suppressive phosphorylation) as well as expression levels of Shc isoforms, total PDH, total Akt and PDK 4 were measured. In addition, phospho/total levels of expression of multiple other members of insulin signaling pathway were measured and the data were consistent with increased metabolic insulin signal flow in Shc silenced cells.

Fasted Blood Glucose Measurements for FIG. 2G:

Mice maintained on HFD for indicated time were food deprived for four hours and blood glucose was measured.

Example 3. Shc KO Mice have Decreased White Adipose in Multiple Fat Pads, Decreased Weight on High-Fat Diets, and Increased Brown Fat ShcKO mice have decreased weight of multiple white fat pads (FIG. 3A). ShcKO mice have decreased weight gain on high-fat diet (FIG. 3B). A likely explanation of increased leanness in ShcKO mice is increased size (FIG. 3C), and metabolic activity (FIG. 3D) of brown fat, and increased brown fat differentiation (FIG. 3E).

Body Composition Protocol for FIG. 3A:

Groups of six mice each genotype: control and ShcKO were sacrificed by cervical dissociation and indicated tissues were weighted, weights were normalized to total body weight of each mouse. Body composition was expressed as weight fold changes of ShcKO over wild type. Data statistically significant under Alfa 5% and with fold changes bigger than 1.2 was considered biologically significant.

Weight Gain Test (WGT) on HFD for FIG. 3B:

Groups of fourteen mice of each genotype were started on HFD at 3 month of age and body weights were measured weekly.

Morphological Study of Brown Fat for FIG. 3C:

Groups of five mice each genotype were sacrificed at 18 month of age and brown fat pads were extracted and stained with hematoxylin-eosin stain, sectioned at 100 um and pictures were taken at magnification of 400×. Obviously, ShcKO mice had bigger brown adipocytes. Cell sizes were measured in a double blind protocol using ImageJ software on five random sections of each mouse and the size distribution was analyzed (25 sections for each genotype total), ShcKo mice had statistically significant increase in number of bigger BAT cells and reduced number of smaller ones.

Western Blot Protocol for FIG. 3D:

BAT fat pads were extracted from six hours fasted Control and ShcKO mice (five mice per group) and protein was extracted as described above. Western blots were performed with indicated antibody as described previously. In FIG. 3D, Shc isoforms expression, VDAC, UCP1, MnSOD, Cyt-c, UCP3 are presented, but expression levels of most metabolic enzymes was also measured, such as ACAA1, ACAA2, GCK, GCKR, HK, PK, PCX, CPT2, VLCAD, MCAD, ETF, PDH/P-PDH, ME1, ACLY, CPS, GS, GSK, P-AMPK, HSL, P-HSL, PDK1, PDK4, PFK, PKM, FOXO/P-FOXO and others (not shown). Consistently, expression of most of the metabolic enzymes was significantly increased in BAT fat of ShcKO mice.

Q-RT-PCR Protocol for FIG. 3E:

The extent of brown fat differentiation was measured by QRTPCR of the differentiation markers prdm16, elovl3, and BMP7, and was found to be more differentiated in ShcKO mice. Total RNA was extracted from BAT tissue of Control and ShcKO mice with TriZol reagent followed by purification with Qiagen RNA-easy mini-kit according to manufacturer instructions. Equal RNA amounts were added to Superscript III First Strand reverse transcriptase reaction mixture (Invitrogen) with oligo-(dT) primer. The resulting templates were subject to Syber Green-based quantitative PCR using specific primers, listed in the table below, and Platinum-Taq DNA polymerase (Invitrogen). Only experiments with a single melting peak were considered for analysis. Amplification ob beta-actin was used as an intrinsic cDNA amount normalization control. Five mice each genotype were analyzed. Reaction qualities were verified by gel electrophoresis. PCR was carried out using LightCycler480 Real time PCR instrument and LightCycler480 analysis software (Roche). Data were first normalized to the expression levels of beta-actin for each sample, than expressed as a ratio to the mean of Control. Results for the BAT markers: Prdm16, Elovl3 and BMP7 are presented. The data were consistent with Western Blots results and together supported the idea of increased BAT differentiation in ShcKO mice. Primers were as follows:

| | | |
|---|---|---|
| ELOVL3-F: | ATGAACTTTGGCGTCCATTC | (SEQ ID NO: 1) |
| ELOVL3-R: | CTTTCTCCTGCCTCCAGATG | (SEQ ID NO: 2) |
| Prdm16-F: | CAGCACGGTGAAGCCATTC | (SEQ ID NO: 3) |
| Prdm16-R: | GCGTGCATCCGCTTGTG | (SEQ ID NO: 4) |
| BMP7-F: | CCTGTCCATCTTAGGGTTGC | (SEQ ID NO: 5) |
| BMP7-R: | GCCTTGTAGGGGTAGGAGAAG | (SEQ ID NO: 6) |
| UCP1-F: | GATGGTGAACCCGACAACTT | (SEQ ID NO: 7) |
| UCP1-R: | CTGAAACTCCGGCTGAGAAG | (SEQ ID NO: 8) |

Example 4. A High-Throughput Screen for Insulin-Sensitizers Based on Insulin-Dependent Activation of Akt Drugs were screened by in-cell western blot (ICWB) for their ability to stimulate phospho-Akt activation in the presence of trace or 10 nM insulin (FIG. 4A). Cells in wells were treated with drugs, and the activity (phosphorylation) of Akt was determined by a phospho-Akt specific antibody. In FIG. 4A, low insulin was given and drugs a, b, c, stimulated Akt activation. In FIG. 4B, 10 nM insulin was given and a, b, and c stimulated signaling over background, and d and e inhibited. FIG. 4C shows the strategy for screening drugs for Shc inhibitors, through a phospho-activation of Akt. Drugs were primarily screened for their ability to promote insulin-dependent stimulation of (phospho) Akt, then secondarily screened for lack of activity to stimulate (phospho) Erk, or a high Akt/Erk ratio. Such drugs are expected to cause insulin sensitivity, resistance to obesity, and longevity. Some drugs having these desired characteristics are Shc inhibitors.

Primary ICWB was Performed as Follows:

FL83B cells were seeded on 384 well plates, 10,000 cells per well in F-12 media supplemented with 10% FBS and 25 mM glucose; 48 hours later the media was replaced with F-12, 25 mM glucose without FBS for sixteen hours; cells were supplemented with assigned drug at desired concentration for 1 hour in duplicate and then, the cells were stimulated with desired concentration of insulin for ten minutes for Akt activation and fifteen minutes for ERK activation measurements. After that time the media was removed and replaced with fixing solution of 5% Formaldehyde in PBS, pH=7.4, 30 minutes later, the fixing solution was replaced with the permeabilization buffer, 0.1% triton X100 in PBS for 40 minutes. Blocking was performed with Li-Cor Odyssey blocking buffer (Li-Cor Biosciences, Inc., Lincoln, Nebr.) and the primary antibodies were allowed to hybridize for one hour at room temperature, followed by tree washes with 0.1% tween-20 in PBS. The rabbit monoclonal anti phospho (Ser437)-Akt antibody and rabbit monoclonal anti phospho (Thr202/Tyr204)-ERK antibodies were from Cell Signaling Technology (Danvers, Mass.), mouse monoclonal anti-tubulin antibodies were form Sigma (St. Louis, Mo.). The secondary antibodies were from Li-Cor Biosciences and they were labeled with the IR-dyes 700 for goat anti-rabbit and 800 for goat anti-mouse. After the incubation with the secondary antibodies for one hour at room temperature, the wells were washed again two times with the 0.1% tween-20 in PBS and scanned on the Li-Cor Odyssey infrared scanner; images were analyzed with the Li-Cor Odyssey software. No-primary antibody wells were used to subtract the background. PI3K inhibitor wortmannin was used to abolish the insulin effect on Akt activation and served as a negative control. Phospho-Akt, Phospho-ERK signals than were normalized by tubulin signals in each well and the densitometric results were analyzed to identify drugs which improved metabolic insulin sensitivity without inducing the mitogenic ERK activation.

Secondary Drug Screening Protocol for FIGS. 4A-C:

ICWB was performed analogously as described above, but drugs were used at seven concentrations of 0.01, 0.1, 1, 2.5, 5, 7.5 and 10 µM in duplicate and insulin was used at two concentrations of 1 nM and 10 nM. The levels of insulin-dependent activation of Akt and ERK were measured with appropriate antibody and normalized to tubulin expression in each well. The drugs were arranged into a megatable and sorted by fold change dependent score of significant improvements of P-Atk signal over P-ERK.

Example 5. Additional Screening Assays

After the high-throughput screening, insulin-sensitizing drugs were further tested and refined in the following ways. The interaction of Shcs, mitochondria and insulin sensitivity is described in FIG. 5B. To refine which of the insulin-sensitizers were Shc inhibitors, drugs were further tested for their ability to stimulate phospho-Akt vs. phospho-Erk pathways (as expected of a Shc inhibitor, because we have previously shown that Shcs function as repressors of insulin signaling, FIGS. 4A-C,FIG. 5B). In addition, Western blots of phosphorylation state (Akt, Erk, AMPK, AS160) were carried out. In addition, we carried out several mitochondrial-based assays, which demonstrated that a large fraction of insulin-sensitizers affect mitochondrial function, whereas mitochondrial effects were much less frequent in the non-insulin sensitizing drugs (not shown here). Blanks on FIG. 5A signify no effect. In addition to inhibiting IRS1 activity, Shcs also stimulate mitochondrial function (FIG. 5B). Thus Shc inhibition alters mitochondrial function, and stimulates AMPK. Stimulation of AMPK is known to inhibit mTOR, and active mTOR inhibits glucose metabolism by inhibiting IRS and Akt. Thus, Shc inhibitors directly stimulate IRS1, and also indirectly stimulate IRS1 and Akt, through repression of mitochondrial function, which stimulates AMPK, which represses mTOR, thus reversing mTORs repressive effects on IRS1 and Akt.

As proof of validity of the screening assay, known anti-diabetic molecules (metformin and acarbose), scored in the top 35 out of 1689 molecules, as did the known Src inhibitor SrcI-1.

So as described in FIGS. 5A-C, drugs were further validated by several additional assays, including: 1) a Western-based phospho-Akt assay (columns 2-4); 2) a Western-based phospho-Erk assay (columns 5-7); a mitochondrial $O_2$ consumption assay (column 8-9), an ATP synthesis assay (column 10), a diamide-based mitochondrial oxidation assay (column 11); a high-throughput phospho-AMP kinase assay (column 12); a Western-based phospho-AMP kinase assay (column 13-14); and a Western-based AS160 assay (column 15-16). It is notable that every single insulin sensitizer was significantly altered for one or more of the 7 assays of mitochondrial function, including 2 and 24 h mitochondrial $O_2$ consumption, mitochondrial ATP synthesis, mitochondrial oxidation sensitivity, HTS AMPK activity in low serum, and Western AMPK activity in high serum. Thus the data support the insulin-sensitization mechanism Shc inhibition→IRS1 stimulation, and also Shc inhibition→altered mitochondrial function→increased AMPK→repression of mTOR→increased insulin sensitization.

Western Blot Protocol of Phospho-Akt (Columns 2-4) and Phospho-Erk (Columns 5-7).

As explained above and in Example 4, Western blots of phospho-Akt and phospho-Erk are a more accurate and precise and quantitative measure of Akt phosphorylation than ICWB measurements. Insulin-dependent phospho-Akt is a direct measurement of insulin sensitivity, and we expect that Shc inhibitors will stimulate phospho-Akt more than phospho-Erk. All of the drugs listed in FIG. 5A stimulated insulin-dependent phospho-Akt at some concentration. Method. Mouse liver cells FL83B were plated at density of 400.000 cells per well of 6 well plate and cultivated for 48 hours, media was changed to DMEM, 25 mM glucose serum free and 16 hours later the cells were treated with drug at the indicated concentration for one hour. Control wells were treated with the vehicle (DMSO), in certain control wells the metabolic (Akt) insulin signaling was blocked with wortmannin. The cells were induced with indicated concentration of insulin for 10 minutes, total protein was extracted and the Western Blots were performed with indicated antibody as described above.

Mitochondrial $O_2$ consumption protocol (columns 8-9). As described above, inhibitors or stimulators of mitochondrial O2 consumption, if they decrease ATP synthesis and thus stimulate AMPK activity, will repress mTOR and thus sensitize to insulin. Also, Shc stimulates mitochondrial function, so Shc inhibitors should inhibit mitochondrial function. Method. Before initiating the assay, cell density was determined using the Vi-Cell counter (Beckman Coulter), and 70,000 RGC5 cells per well were aliquoted into 384-well oxygen biosensor plates (Becton Dickinson Probe) in 90 µL of phenol-red free growth media (DMEM supplemented with 10% fetal bovine serum), and the cells were allowed to attach for 20-30 min. Ten µL of test compounds (10 mM stock in DMSO) or vehicle were dispensed into wells after an intermediate dilution in PBS, giving a final DMSO concentration of 0.1%. Test compounds were all tested at 3 and 10 µM final assay concentrations. There were 6 negative control (DMSO vehicle only) and 6 positive control (5 µM FCCP) wells on each plate. Plates were incubated at 37° C. under a 5% $CO_2$ for 2 or 24 h and then fluorescence was measured (485 nm excitation; 630 nm emission) (BMG Labtech, Germany). The statistical significance of the data was determined with a two-tailed Student t test (p-value <0.05).

Mitochondrial ATP synthesis protocol (column 10). As explained above, a decrease in ATP synthesis is known to stimulate AMPK, which inhibits mTOR, thus resulting in insulin sensitization. ATP levels were measured by a luminometric assay following the manufacturer's protocol. Method. Briefly, cells were permeabilized with digitonin and incubated in a buffer containing 0.25M sucrose, 20 mM MOPS, 1 mM EDTA, 5 mM inorganic phosphate, 0.1% BSA fatty acid free, and 1 mM ADP, pH 7.4. At a concentration of 0.1 micromolar rotenone, to measure complex I-V activity, 5 mM pyruvate (glutamate) and 1 mM malate were added to the permeabilized cells and 10 µg/ml oligomycin was also added to determine the amount of non-mitochondrial ATP production in each sample. ATP production was kinetically measured by a luminometric assay (Roche) and non-mitochondrial ATP production was subtracted from the overall production. As a normalization marker, protein levels were measured using the Bradford protein assay (Bio-Rad).

Mitochondrial Oxidation (column 11) Diamide Screening Assay. We have previously shown that diamide sensitivity is a measure of mitochondrial oxidant sensitivity. Others have shown that mitochondrial antioxidant protecting is linked to mitochondrial bioenergetics function. Thus, drugs that de-energize mitochondria cause sensitization to the mitochondrial oxidant diamide. Drugs that de-energize mitochondria increase AMPK, repressing mTOR, and increasing insulin sensitivity. Method. Fibroblasts were grown in MEM media (Gibco) supplemented with 15% fetal bovine serum in t225 tissue culture flasks and kept below 70% confluency. Cells were trypsinized and density determined using a Vi-Cell counter (Beckman Coulter). 5,000 fibroblast cells were then aliquoted into 96-well poly-d-lysine coated black/clear culture plates (Becton Dickinson) in growth media without antibiotics in a volume of 180 microliters. Cells were allowed to adhere for 3-4 hours at 37 C. Drugs (10 mM stock in DMSO) were dispensed into assay plate wells after an intermediate dilution in PBS, giving a final DMSO concentration of 0.1% using an electronic multichannel pipetter (BioHit). Pharmakon drug library consisted of 1600 compounds (Microsource) in 96 well plates at stock concentration of 10 mM in DMSO. Test compounds were all be tested at 10 micromolar final assay concentration in primary screen. 8 wells each of 300 micromolar Dithiothreitol (Sigma) or 0.1% DMSO were used as positive or negative controls respectively. Cells were then incubated at 37 C with 5% CO2 overnight. After 24 hours, Diamide (Sigma) was added to all wells at a final concentration of 125 micromolar from a 100 millimolar stock solution prepared in dmso and allowed to incubate at 37 C with 5% CO2 overnight (14-18 hours). Plates were then washed with PBS, supplemented with 1 uM Calcein AM (Molecular Probes) and incubated at RT for 45 min. Cells are again washed with PBS to remove residual dye, and read on BMG PolarStar Optima with 485 excitation and 520 emission wavelengths (BMG LabTech).

Phospho-AMPK Activation in Cell Western Blot High-Throughput Screening Assay (Column 12).

As explained above, mitochondrial de-energization leads to decreased mitochondrial production of ATP, increased AMP, and activation of AMP kinase, which represses mTOR and increases insulin sensitivity (FIG. 5B). Method. Analogous to the In Cell Western Blot described in example 4 for phospho-Akt and phospho-Erk, cells were screened for activation of phospho-AMPK. Cells were glucose-starved or glucose- and serum-starved for 16 hr to activate phospho-AMPK. In Cell Western Blots (ICWB) were performed exactly as described in example 4, with phospho-AMPK antibody. Seven concentrations of drugs from 0.1 to 10 micromolar were used.

Phospho-AMPK activation (column 13-14) and phospho-AS160 activation (column 15-16) measurement by standard Western protocol. As described above for Example 5, columns 2-7, we carried out a western protocol, but used antibody to phospho-AMP kinase, or phospho-AS160.

Discussion. Aside from finding 35 insulin sensitizers in the screen of 1689 drugs in terms of insulin-dependent phosphoAkt activation, we also further refined the drugs with respect to their effects on mitochondrial function. As shown in FIG. 5C, a very large fraction of the insulin sensitizers stimulated AMP kinase, indicating an effect on mitochondrial function. We followed up this with several other tests of mitochondrial function, including O2 consumption, ATP synthesis, protection from mitochondrial oxidation, and AS160 activation, and every single drug has an effect on at least one of these mitochondrial parameters. This supports a Shc and mitochondrial mechanism of insulin sensitization presented in FIG. 5B, i.e. Shc→mitochondria→AMPK→mTOR inhibition→insulin sensitivity.

Example 6. Src I-1 Significantly Decreased Basal Blood Glucose and Increased Insulin Sensitivity In-Vivo and Decreases Shc Activation The Src-inhibitor Src I-1 was identified by the screening in FIGS. 5A-C. Src I-1 stimulates insulin-dependent P-Akt signaling (FIG. 6A), but, at the same time decreased Erk activation, thus increasing the P-Akt/P-Erk ratio (FIG. 6B). Src I-1 inhibited phospho-Shc activation in dose-dependent manner (FIG. 6D). A low dose of SrcI-1 (2.5 mg/kg) administered to mice for 4 days I.P. significantly decreased basal blood glucose (FIG. 6E), and increased insulin sensitivity in-vivo (FIG. 6E).

Western Blot Protocol for FIG. 6 A, B, C:

Mouse liver cells FL83B were plated at density of 400.000 cells per well of 6 well plate and cultivated for 48 hours, media was changed to DMEM, 25 mM glucose serum free and 16 hours later the cells were treated with drug at the indicated concentration for one hour. Control wells were treated with the vehicle (DMSO), in certain control wells the metabolic (Akt) insulin signaling was blocked with wortmannin. The cells were induced with indicated concentration of insulin for 10 minutes, total protein was extracted and the Western Blots were performed with indicated antibody as described above. The figure shows the drug was improving metabolic insulin signaling and at the same time suppressing the mitogenic signal flow, representing a Shc-inhibitory drug mechanism.

In-Vivo Drugs Testing to Improve the Insulin Sensitivity of Periphery for FIG. 6D, E:

Groups of mice, ten for the experimental drug treatment and 14 for the placebo treatment were subject for I.P. administration of a drug or placebo solutions daily during four days. Acarbose, a known drug which decreases blood glucose concentration was used as a control. The insulin tolerance test, ITT was performed on the mice as described previously, in Example 2.

Example 7. Idebenone Significantly Increases Insulin Sensitivity In Vitro and In Vivo, and Decreases Shc Activation Idebenone was also identified in the primary screen by increased P-Akt/P-Erk ratio as described in Example 4, and also increased insulin-dependent phospho-Akt activation in a dose-dependent manner (FIG. 7AB). In addition, idebenone decreased phospho-Shc in a dose-dependent manner (FIG. 7CD). When administered to mice PO at a dose of 20 and 50 mg/kg, idebenone increased insulin sensitivity in vivo (FIG. 7E). Methods. Western Blots were exactly as described in example 6, and insulin tolerance test exactly as described in example 6.

The examples and embodiments described herein are for illustrative purposes only and that various modifications or changes in light thereof are to be included within the spirit and purview of this application and scope of the appended claims. Each embodiment, aspect, element, feature, step or the like can be used in combination with any other unless the context requires otherwise. All publications (including accession numbers, websites and the like), patents, and patent applications cited herein are hereby incorporated by reference in their entirety for all purposes to the same extent as if so individually denoted. To the extend a reference, such as an accession number or catalog number is associated with different content at different times, the version in effect at the effective filing date of the application is meant. Effective filing date means the actual filing date or earlier filing date in which such reference was cited.

SEQUENCE LISTING

SEQ ID NO: 1
ELOVL3-F
ATGAACTTTGGCGTCCATTC

SEQ ID NO: 2
ELOVL3-R
CTTTCTCCTGCCTCCAGATG

SEQ ID NO: 3
Prdm16-F
CAGCACGGTGAAGCCATTC

SEQ ID NO: 4
Prdm16-R
GCGTGCATCCGCTTGTG

SEQ ID NO: 5
BMP7-F
CCTGTCCATCTTAGGGTTGC

SEQ ID NO: 6
BMP7-R
GCCTTGTAGGGGTAGGAGAAG

SEQ ID NO: 7
UCP1-F
GATGGTGAACCCGACAACTT

SEQ ID NO: 8
UCP1-R
CTGAAACTCCGGCTGAGAAG

---

What is claimed is:

1. A method of treating impaired insulin sensitivity, impaired glucose tolerance or obesity, comprising administering to a subject having the impaired insulin sensitivity, glucose tolerance or obesity an effective regime of idebenone as sole active agent, or a pharmaceutically acceptable salt thereof, thereby treating impaired insulin sensitivity, impaired glucose tolerance or obesity.

2. The method of claim 1, wherein the subject has type 2 diabetes.

3. The method of claim 1, wherein the subject has a body mass index of at least 30.

4. The method of claim 1, wherein the subject has or is at risk of metabolic syndrome.

5. The method of claim 4, wherein the subject has diabetes type 2.

6. The method of claim 4, wherein the subject is obese.

7. The method of claim 4, wherein the subject has impaired insulin sensitivity and glucose tolerance.

8. The method of claim 4, wherein the subject has hyperglycemia.

9. The method of claim 4, wherein the subject has dyslipidemia.

10. The method of claim 4, wherein the subject has microalbuminuria.

11. A method of treating impaired insulin sensitivity, impaired glucose tolerance or obesity, comprising co-administering to the subject having the impaired insulin sensitivity, glucose tolerance or obesity an effective regime of idebenone and Src I-1, or a pharmaceutically acceptable salt thereof, thereby treating impaired insulin sensitivity, impaired glucose tolerance or obesity.

12. The method of claim 11, wherein the subject has type 2 diabetes.

13. The method of claim 11, wherein the subject has a body mass index of at least 30.

14. The method of claim 11, wherein the subject has or is at risk of metabolic syndrome.

15. The method of claim 14, wherein the subject has diabetes type 2.

16. The method of claim 14, wherein the subject is obese.

17. The method of claim 14, wherein the subject has impaired insulin sensitivity and glucose tolerance.

18. The method of claim 14, wherein the subject has hyperglycemia.

19. The method of claim 14, wherein the subject has dyslipidemia.

20. The method of claim 14, wherein the subject has microalbuminuria.

* * * * *